(12) United States Patent
Dombroski et al.

(10) Patent No.: US 7,037,923 B2
(45) Date of Patent: *May 2, 2006

(54) ALKYL-[4-(TRIFLUOROPHENYL)-OXAZOL-5-YL]-TRIAZOLO-PYRIDINES

(75) Inventors: Mark A. Dombroski, Waterford, CT (US); Michael A. Letavic, Mystic, CT (US); Kim F. McClure, Mystic, CT (US)

(73) Assignee: Pfizer, Inc., New York, NY (US)

( * ) Notice: Subject to any disclaimer, the term of this patent is extended or adjusted under 35 U.S.C. 154(b) by 199 days.

This patent is subject to a terminal disclaimer.

(21) Appl. No.: 10/649,265

(22) Filed: Aug. 27, 2003

(65) Prior Publication Data

US 2004/0077682 A1    Apr. 22, 2004

Related U.S. Application Data

(60) Provisional application No. 60/407,089, filed on Aug. 30, 2002.

(51) Int. Cl.
*A61K 31/44* (2006.01)
*C07D 471/02* (2006.01)

(52) U.S. Cl. .................... 514/303; 546/119
(58) Field of Classification Search .......... 546/119; 514/303
See application file for complete search history.

(56) References Cited

U.S. PATENT DOCUMENTS

| | | | | |
|---|---|---|---|---|
| 5,716,955 | A | 2/1998 | Adams et al. | 514/235.8 |
| 5,716,972 | A | 2/1998 | Adams et al. | 514/341 |
| 5,717,100 | A | 2/1998 | Selnick et al. | 546/194 |
| 5,756,499 | A | 5/1998 | Adams et al. | 514/235.8 |
| 5,777,097 | A | 7/1998 | Lee et al. | 536/24.31 |
| 6,288,062 | B1 | 9/2001 | Adams et al. | 514/236.8 |
| 6,696,464 | B1 * | 2/2004 | McClure et al. | 514/303 |

FOREIGN PATENT DOCUMENTS

| | | |
|---|---|---|
| EP | 1247810 | 10/2002 |
| WO | 9901449 | 1/1999 |
| WO | 9961440 | 12/1999 |
| WO | 0006563 | 2/2000 |
| WO | 0031065 | 6/2000 |
| WO | 0035911 | 6/2000 |
| WO | 0040243 | 7/2000 |
| WO | 0041698 | 7/2000 |
| WO | 0063204 | 10/2000 |
| WO | 0272576 | 9/2002 |
| WO | 0272579 | 9/2002 |

OTHER PUBLICATIONS

The Journal of Biological Chemistry, vol. 271, No. 40, pp. 24313-24316 (1996).
Bioorganic & Medicinal Chemistry Letters, 10, pp. 2047-2050 (2000); and.
Bioorganic & Medicinal Chemistry Letters, 11, pp. 9-12 (2001).

* cited by examiner

*Primary Examiner*—Patricia L. Morris
(74) *Attorney, Agent, or Firm*—Julie M. Lappin; Charles Ashbrook; Christopher W. Slavinsky

(57) ABSTRACT

The present invention relates to novel alkyl-[4-(trifluorophenyl)-oxazol-5-yl]-triazolo-pyridines, to intermediates and methods for their preparation, to pharmaceutical compositions containing them and to their medicinal use. The compounds of the present invention are potent inhibitors of MAP kinases, preferably p38 kinase. They are useful in the treatment of inflammation, osteoarthritis, rheumatoid arthritis, cancer, reperfusion or ischemia in stroke or heart attack, autoimmune diseases and other disorders.

11 Claims, No Drawings

ALKYL-[4-(TRIFLUOROPHENYL)-OXAZOL-5-YL]-TRIAZOLO-PYRIDINES

The present invention relates to novel alkyl-[4-(trifluorophenyl)-oxazol-5-yl]-triazolo-pyridines, to intermediates and methods for their preparation, to pharmaceutical compositions containing them and to their medicinal use. The compounds of the present invention are potent inhibitors of MAP kinases, preferably p38 kinase. They are useful in the treatment of inflammation, osteoarthritis, rheumatoid arthritis, cancer, reperfusion or ischemia in stroke or heart attack, autoimmune diseases and other disorders.

Intracellular signal transduction is the means by which cells respond to extracellular stimuli. Regardless of the nature of the cell surface receptor (e.g. protein tyrosine kinase or seven-transmembrane G-protein coupled), protein kinases and phosphatases along with phopholipases are the essential machinery by which the signal is further transmitted within the cell [Marshall, J. C., *Cell*, 80, 179–278 (1995)]. Protein kinases can be categorized into five classes with the two major classes being, tyrosine kinases and serine/threonine kinases depending upon whether the enzyme phosphorylates its substrate(s) on specific tyrosine(s) or serine/threonine(s) residues [Hunter, T., *Methods in Enzymology* (Protein Kinase Classification), p. 3, Hunter, T.; Sefton, B. M.; eds. vol. 200, Academic Press; San Diego, 1991].

For most biological responses, multiple intracellular kinases are involved and an individual kinase can be involved in more than one signaling pathway. These kinases are often cytosolic and can translocate to the nucleus or the ribosomes where they can affect transcriptional and translational events, respectively. The involvement of kinases in transcriptional control is presently much better understood than their effect on translation as illustrated by the studies on growth factor induced signal transduction involving MAP/ERK kinase [Marshall, C. J., *Cell*, 80, 179 (1995); Herskowitz, I., *Cell*, 80, 187 (1995); Hunter, T., *Cell*, 80, 225 (1995); Seger, R., and Krebs, E. G., *FASEB J.*, 726–735 (1995)].

While many signaling pathways are part of normal cell homeostasis, numerous cytokines (e.g., IL-1 and TNF) and certain other mediators of inflammation (e.g., COX-2, and iNOS) are produced only as a response to stress signals such as bacterial lipopolysaccharide (LPS). Early evidence suggesting that the signal transduction pathway leading to LPS-induced cytokine biosynthesis involved protein kinases came from studies of Weinstein [Weinstein, et al., *J. Immunol*, 151, 3829(1993)] but the specific protein kinases involved were not identified. Working from a similar perspective, Han [Han, et al., *Science* 265, 808(1994)] identified murine p38 as a kinase which is tyrosine phosphorylated in response to LPS. Additional evidence of the involvement of the p38 kinase in LPS-stimulated signal transduction pathway leading to the initiation of proinflammatory cytokine biosynthesis was provided by the discovery of p38 kinase (MAPK14, CSBP 1 and 2) by Lee [Lee; et al,. *Nature*, 372, 739(1994)] as the molecular target for a novel class of anti-inflammatory agents. Thus, compounds which inhibit p38 will inhibit IL-1 and TNF synthesis in human monocytes. Such results have been reported by [Lee, et al., *Int. J. Immunopharmac.*, 10(7), 835(1988)] and [Lee; et al., *Annals N.Y. Acad. Sci.*, 696, 149(1993)].

It is now accepted that CSBP/p38 is one of several kinases involved in a stress-response signal transduction pathway which is parallel to and largely independent of the analogous mitogen-activated protein kinase (MAP) kinase cascade. Stress signals, including LPS, pro-inflammatory cytokines, oxidants, UV light and osmotic stress, activate kinases upstream from CSBP/p38 which in turn phosphorylate CSBP/p38 at threonine 180 and tyrosine 182 resulting in CSBP/p38 activation. MAPKAP kinase-2 and MAPKAP kinase-3 have been identified as downstream substrates of CSBP/p38 which in turn phosphorylate heat shock protein Hsp 27. It is now known that MAPKAP-2 is essential for LPS induced TNFα biosynthesis [Kotlyarov, et al., *Nature Cell Biol.*, 1, 94 (1999), see also Cohen, P., *Trends Cell Biol.*, 353–361(1997)].

In addition to inhibiting IL-1 and TNF, CSBP/p38 kinase inhibitors also decrease the synthesis of a wide variety of pro-inflammatory proteins including, IL-6, IL-8, GM-CSF and COX-2. Inhibitors of CSBP/p38 kinase have also been shown to suppress the TNF-induced expression of VCAM-1 on endothelial cells, the TNF-induced phosphorylation and activation of cytosolic PLA2 and the IL-1 stimulated synthesis of collagenase and stromelysin. These and additional data demonstrate that CSBP/p38 is involved not only cytokine synthesis, but also in cytokine signaling [CSBP/p38 kinase reviewed in Cohen, P., *Trends Cell Biol.*, 353–361 (1997)].

Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation [See, e.g.,. Dinarello et al., Rev. Infect. Disease, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease, tuberculosis, atherosclerosis, muscle degeneration, cachexia, psoriatic arthritis, Reiter's syndrome, rheumatoid arthritis, gout, traumatic arthritis, rubella arthritis, and acute synovitis. Other studies also link IL-1 activity to diabetes and pancreatic β cells, Dinarello, *J. Clinical Immunology*, 5 (5), 287–297 (1985).

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft vs. host reaction, allograft rejections, fever and myalgias due to infection, such as influenza, cachexia secondary to infection or malignancy, cachexia secondary to acquired immune deficiency syndrome (AIDS), AIDS, ARC (AIDS related complex), keloid information, scar tissue formation, Crohn's disease, ulcerative colitis, or pyrosis.

Interleukin-8 (IL-8) is a chemotactic factor produced by several cell types including mononuclear cells, fibroblasts, endothelial cells, and keratinocytes. Its production from endothelial cells is induced by IL-1, TNF, or lipopolysaccharide (LPS). IL-8 stimulates a number of functions in vitro. It has been shown to have chemoattractant properties for neutrophils, T-lymphocytes, and basophils. In addition it induces histamine release from basophils from both normal and atopic individuals as well lysosomal enzyme release and respiratory burst from neutrophils. IL-8 has also been shown to increase the surface expression of Mac-1 (CD11b/CD18) on neutrophils without de novo protein synthesis, this may contribute to increased adhesion of the neutrophils to vascular endothelial cells. Many diseases are characterized by massive neutrophil infiltration. Conditions associated with an increase in IL-8 production (which is responsible for chemotaxis of neutrophils into the inflammatory site) would benefit by compounds which are suppressive of IL-8 production.

Human interleukin-18 (IL-18) is another member of the interleukin family that has recently been identified. IL-18 is a cytokine that is synthesized as a biologically inactive 193 amino acid precursor protein (Ushio et al., J. Immunol., 15 6:4274, 1996). Cleavage of the precursor protein, for example by caspase-1 or caspase-4, liberates the 156 amino acid mature protein (Gu, et al., *Science*, 275:206, 1997; Ghayur, et al., *Nature*, 386:619, 1997), which exhibits biological activities that include the costimulation of T cell proliferation, the enhancement of NK cell cytotoxicity, the induction of IFN-γ production by T cells and NK cells, and the potentiation of T helper type I (Th I) differentiation (Okamura, et al., *Nature*, 378:88, 1995; Ushio, et al., *J. Immunol.*, 156:4274, 1996; Micallef, et al., *Eur. J. Immunol.*, 26:1647, 1996; Kohno, et al., *J. Immunol.*, 158:1541, 1997; Zhang, et al., *Infect. Immunol.*, 65:3594, 1997; Robinson, et al., *Immunol.*, 7:571, 1997). In addition, IL-18 is an efficacious inducer of human monocyte proinflammatory mediators, including IL-8, tumor necrosis factor-α, and prostaglandin E2 (PGE2) (Ushio, S., et al., *J. Immunol.*, 156: 4274–4279, 1996; Puren, A. J., et al., *J. Clin. Invest.*, 10:711–721, 1997).

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

Inhibition of signal transduction via CSBP/p38, which in addition to IL-1, TNF and IL-8 described above is also required for the synthesis and/or action of several additional pro-inflammatory proteins (i.e., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for CSBP/p38 kinase inhibitors [Badger, et al., *J. Pharm. Exp. Thera.*, 279 (3); 1453–1461. (1996); Griswold, et al., *Pharmacol. Comm.*, 7, 323–229 (1996)].

There remains a need for treatment, in this field, for compounds which are cytokine suppressive anti-inflammatory drugs, i.e., compounds which are capable of inhibiting the MAPK14/CSBP/p38/RK kinase.

Other kinases differentially affected by the compounds of the present invention include: Extracellular signal regulated kinase-1 (ERK1 or MAPK3), Extracellular signal regulated kinase-2 (ERK2 or MAPK2), Extracellular signal regulated kinase-3 (ERK3 or MAPK6), Extracellular signal regulated kinase-5 (ERK5 or MAPK7), Extracellular signal regulated kinase-6 (ERK6 or MAPK12), MAPK1, MAPK4, MAPK8, MAPK9, MAPK10, MAPK11, and MAPK13.

MAPK14/CSBP/p38/RK kinase inhibitors are well known to those skilled in the art. U.S. Provisional Applications 60/274791, 60/274840 and 60/281331, filed Mar. 9, 2001, Mar. 9, 2001 and Apr. 4, 2001, respectively, and entitled "Novel Antiinflammatory Compounds," "Novel Triazolopyridine Antiinflammatory Compounds" and "Novel Benzotriazole Antiinflammatory Compounds," respectively, refer to certain inhibitors of MAP kinases, preferably p38 kinase. International Patent Publication WO 00/40243, published Jul. 13, 2000, refers to pyridine substituted pyridine compounds and states that these compounds are p38 inhibitors. International Patent Publication WO 00/63204, published Oct. 26, 2000, refers to substituted azole compounds and states that these compounds are p38 inhibitors. International Patent Publication WO 00/31065, published Jun. 2, 2000, refers to certain heterocyclic compounds and states that these compounds are p38 inhibitors. International Patent Publication WO 00/06563, published Feb. 10, 2000, refers to substituted imidazole compounds and states that these compounds are p38 inhibitors. International Patent Publication WO 00/41698, published Jul. 20, 2000, refers to certain ω-carboxy aryl substituted diphenyl urea compounds and states that these compounds are p38 inhibitors. U.S. Pat. No. 6,288,062 refers to certain substituted oxazole compounds and states that these compounds are p38 inhibitors. U.S. Pat. No. 5,716,955 refers to certain substituted imidazole compounds and states that these compounds are p38 inhibitors. U.S. Pat. No. 5,716,972 refers to certain pyridinyl substituted imidazole compounds and states that these compounds are p38 inhibitors. U.S. Pat. No. 5,756,499 refers to certain substituted imidazole compounds and states that these compounds are p38 inhibitors.

SUMMARY OF THE INVENTION

The present invention relates to a compound of the formula

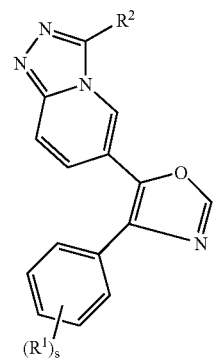

wherein $R^1$ is fluoro;
s is three;
$R^2$ is $(C_1–C_6)$alkyl optionally substituted by one or two moieties independently selected from the group consisting of halo, $(C_1–C_6)$alkyl, hydroxy, $(C_1–C_6)$alkoxy, and $(C_1–C_6)$alkyl-(C=O)—O—;
or pharmaceutically acceptable salts and prodrugs thereof.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the chloride, bromide, iodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The compounds of this invention include all stereoisomers (e.g., cis and trans isomers) and all optical isomers of compounds of the formula I (e.g., R and S enantiomers), as well as racemic, diastereomeric and other mixtures of such isomers.

The compounds and prodrugs of the present invention can exist in several tautomeric forms, including the enol and imine form, the keto and enamine form and geometric isomers and mixtures thereof. All such tautomeric forms are included within the scope of the present invention. Tautomers exist as mixtures of tautomers in solution. In solid form, usually one tautomer predominates. Even though one tautomer may be described, the present invention includes all tautomers of the present compounds.

The present invention also includes atropisomers of the present invention. Atropisomers refer to compounds of formula I that can be separated into rotationally restricted isomers.

The compounds of this invention may contain olefin-like double bonds. When such bonds are present, the compounds of the invention exist as cis and trans configurations and as mixtures thereof.

As used herein, the term "alkyl," as well as the alkyl moieties of other groups referred to herein (e.g., alkoxy), may be linear or branched (such as methyl, ethyl, n-propyl, isopropyl, n-butyl, iso-butyl, secondary-butyl, tertiary-butyl), and they may also be cyclic (e.g., cyclopropyl or cyclobutyl); optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. The phrase "each of said alkyl" as used herein refers to any of the preceding alkyl moieties within a group such alkoxy, alkenyl or alkylamino. Preferred alkyls include $(C_1-C_4)$alkyl, most preferably methyl.

As used herein, the term "cycloalkyl" refers to a mono or bicyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1–2 double bonds and optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. The phrase "each of said alkyl" as used herein refers to any of the preceding alkyl moieties within a group such alkoxy, alkenyl or alkylamino. Preferred cycloalkyls include cyclobutyl, cyclopentyl and cyclohexyl.

As used herein, the term "halogen" includes fluoro, chloro, bromo or iodo or fluoride, chloride, bromide or iodide.

As used herein, the term "halo-substituted alkyl" refers to an alkyl radical as described above substituted with one or more halogens included, but not limited to, chloromethyl, dichloromethyl, fluoromethyl, difluoromethyl, trifluoromethyl, 2,2,2-trichloroethyl, and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "alkenyl" means straight or branched chain unsaturated radicals of 2 to 6 carbon atoms, including, but not limited to ethenyl, 1-propenyl, 2-propenyl (allyl), iso-propenyl, 2-methyl-1-propenyl, 1-butenyl, 2-butenyl, and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "$(C_2-C_6)$alkynyl" is used herein to mean straight or branched hydrocarbon chain radicals having one triple bond including, but not limited to, ethynyl, propynyl, butynyl, and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "carbonyl" or "(C=O)" (as used in phrases such as alkylcarbonyl, alkyl-(C=O)— or alkoxycarbonyl) refers to the joinder of the >C=O moiety to a second moiety such as an alkyl or amino group (i.e. an amido group). Alkoxycarbonylamino (i.e. alkoxy(C=O)—NH—) refers to an alkyl carbamate group. The carbonyl group is also equivalently defined herein as (C=O). Alkylcarbonylamino refers to groups such as acetamide.

As used herein, the term "aryl" means aromatic radicals such as phenyl, naphthyl, tetrahydronaphthyl, indanyl and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "heteroaryl" refers to an aromatic heterocyclic group usually with one heteroatom selected from O, S and N in the ring. In addition to said heteroatom, the aromatic group may optionally have up to four N atoms in the ring. For example, heteroaryl group includes pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. Particularly preferred heteroaryl groups include oxazolyl, imidazolyl, pyridyl, thienyl, furyl, thiazolyl and pyrazolyl (these heteroaryls are most preferred of the $R^4$, $R^5$, $R^6$ and $R^7$ heteroaryls).

The term "heterocyclic" as used herein refers to a cyclic group containing 1–9 carbon atoms and 1–4 hetero atoms selected from N, O, S or NR'. Examples of such rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl and the like. Examples of such monocyclic saturated or partially saturated ring systems are tetrahydrofuran-2-yl, tetrahydrofuran-3-yl, imidazolidin-1-yl, imidazolidin-2-yl, imidazolidin4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, 1,4-oxazin-2-yl, 1,2,5-oxathiazin-4-yl and the like; optionally substituted by 1 to 3 suitable substituents as defined above such as fluoro, chloro, trifluoromethyl, $(C_1-C_6)$alkoxy, $(C_6-C_{10})$ aryloxy, trifluoromethoxy, difluoromethoxy or $(C_1-C_6)$ alkyl. Preferred heterocyclics include tetrahydrofuranyl, pyrrolidinyl, piperidinyl, piperazinyl and morpholinyl.

A specific embodiment of the present invention are those compounds of formula I wherein $R^2$ is optionally substituted $(C_1-C_4)$alkyl.

Another embodiment of the present invention are those compounds of formula I wherein $R^2$ is $(C_1-C_6)$alkyl optionally substituted with one or two groups independently selected from halo, hydroxy, and $(C_1-C_6)$alkoxy, more preferably wherein $R^2$ is optionally substituted ethyl, isopropyl, isobutyl, t-butyl or sec-butyl.

Another embodiment of the present invention are those compounds of formula I wherein the compound has the formula

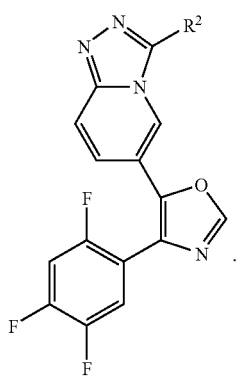

Ia

Another embodiment of the present invention are those compounds of formula I wherein $R^2$ is $(C_1-C_6)$alkyl (more preferably ethyl, isopropyl, isobutyl, t-butyl or sec-butyl), optionally substituted with halo or hydroxy. Most preferably $R^2$ is $(C_1-C_4)$alkyl.

Examples of specific preferred trifluoro compounds of the formula I are the following:
3-Isopropyl-6-[4-(2,4,5-trifluoro-phenyl)-oxazol-5-yl]-[1,2,4]triazolo[4,3-a]pyridine;
3-Isopropyl-6-[4-(2,3,4-trifluoro-phenyl)-oxazol-5-yl]-[1,2,4]triazolo[4,3-a]pyridine;
3-Isopropyl-6-[4-(2,3,5-trifluoro-phenyl)-oxazol-5-yl]-[1,2,4]triazolo[4,3-a]pyridine;
3-Isopropyl-6-[4-(2,4,6-trifluoro-phenyl)-oxazol-5-yl]-[1,2,4]triazolo[4,3-a]pyridine;
3-Isopropyl-6-[4-(3,4,5-trifluoro-phenyl)-oxazol-5-yl]-[1,2,4]triazolo[4,3-a]pyridine; and
3-tert-Butyl-6-[4-(2,4,5-trifluoro-phenyl )-oxazol-5-yl]-[1,2,4]triazolo[4,3-a]pyridine;

Other specific triazolopyridine compounds of formula I include the following:
3-Ethyl-6-[4-(2,4,6-trifluoro-phenyl)-oxazol-5-yl]-[1,2,4]triazolo[4,3-a]pyridine;
3-Isopropyl-6-[4-(3,4,5-trifluoro-phenyl)-oxazol-5-yl]-[1,2,4]triazolo[4,3-a]pyridine;
2-{6-[4-(2,4,5-Trifluorophenyl)-oxazol-5-yl]-[1,2,4]triazolo[4,3-a]pyridin-3yl}-propan-2-ol;
3-Isopropyl-6-[4-(2,3,4-trifluoro-phenyl)-oxazol-5-yl]-[1,2,4]triazolo[4,3-a]pyridine;
3-Tert-butyl-6-[4-(2,4,6-trifluoro-phenyl)-oxazol-5-yl]-[1,2,4]triazolo[4,3-a]pyridine;
3-Methyl-6-[4-(3,4,5-trifluoro-phenyl)-oxazol-5-yl]-[1,2,4]triazolo[4,3-a]pyridine; and
3-Tert-Butyl-6-[4-(2,4,5-trifluoro-phenyl)-oxazol-5-yl]-[1,2,4]triazolo[4,3-a]pyridine.

The present invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

The compounds of Formula I or a pharmaceutically acceptable salt thereof can be used in the manufacture of a medicament for the prophylactic or therapeutic treatment of any disease state in a human, or other mammal, which is exacerbated or caused by excessive or unregulated cytokine production by such mammal's cells, such as but not limited to monocytes and/or macrophages.

Compounds of Formula (I) are capable of inhibiting proinflammatory cytokines, such as IL-1, IL-6, IL-8, IL-18 and TNF and are therefore of use in therapy. IL-1, IL-6, IL-8, IL-18 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Accordingly, the present invention provides a method of treating a cytokine mediated disease which comprises administering an effective cytokine-interfering amount of a compound of Formula (I) or a pharmaceutically acceptable salt thereof.

Certain compounds of Formula (I) are capable of inhibiting inducible pro-inflammatory proteins, such as COX-2, also referred to by many other names such as prostaglandin endoperoxide synthase-2 (PGHS-2) and are therefore of use in therapy. These proinflammatory lipid mediators of the cyclooxygenase (COX) pathway are produced by the inducible COX-2 enzyme. Regulation, therefore of COX-2 which is responsible for these products derived from arachidonic acid, such as prostaglandins, affect a wide variety of cells and tissues. Expression of COX-1 is not effected by compounds of Formula (I). This selective inhibition of COX-2 is accepted as alleviating or sparing ulcerogenic liability associated with inhibition of COX-1 thereby inhibiting prostaglandins essential for cytoprotective effects. Thus inhibition of these pro-inflammatory mediators is of benefit in controlling, reducing and alleviating many of these disease states. Most notably these inflammatory mediators, in particular prostaglandins, have been implicated in pain, such as in the sensitization of pain receptors, or edema. This aspect of pain management, therefore, includes treatment of neuromuscular pain, headache, cancer pain, and arthritis pain. Compounds of Formula (I), or a pharmaceutically acceptable salt thereof, are of use in therapy in a human, or other mammal, by inhibition of the synthesis of the COX-2 enzyme.

Accordingly, the present invention provides a method of inhibiting the synthesis of COX-2 which comprises administering an effective amount of a compound of Formula (I) or a pharmaceutically acceptable salt thereof. The present invention also provides for a method of treatment in a human, or other mammal, by inhibition of the synthesis of the COX-2 enzyme.

In particular, compounds of Formula (I) or a pharmaceutically acceptable salt thereof are of use in the therapy of any disease state in a human, or other mammal, which is exacerbated by or caused by excessive or unregulated IL-1, IL-8 or TNF production by such mammal's cells, such as, but not limited to, monocytes and/or macrophages.

Accordingly, in another aspect, this invention relates to a method of inhibiting the production of IL-1 in a mammal in need thereof which comprises administering to said mammal an effective amount of a compound of Formula (I) or a pharmaceutically acceptable salt thereof.

There are many disease states in which excessive or unregulated IL-1 production is implicated in exacerbating and/or causing the disease. These include rheumatoid arthritis, osteoarthritis, meningitis, ischemic and hemorrhagic stroke, neurotrauma/closed head injury, stroke, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic arthritis, Reiter's syndrome, rheumatoid arthritis, gout, traumatic arthritis, rubella arthritis and acute synovitis. Recent evidence also links IL-1 activity to diabetes, pancreatic β cells disease, and Alzheimer's disease.

Use of a p38 inhibitor for the treatment of p38 mediated disease states, can include, but is not limited to neurodegenerative diseases, such as Alzheimer's disease, Parkinson's disease and multiple sclerosis, etc. In a further aspect, this invention relates to a method of inhibiting the production of TNF in a mammal in need thereof which comprises administering to said mammal an effective amount of a compound of Formula (I) or a pharmaceutically acceptable salt thereof.

Excessive or unregulated TNF production has been implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, stroke, cerebral malaria, chronic obstructive pulmonary disease, chronic pulmonary inflammatory disease, silicosis, pulmonary sarcoidosis, bone resorption diseases, such as osteoporosis, cardiac, brain and renal reperfusion injury, graft vs. host reaction, allograft rejections, fever and myalgias due to infection, such as influenza, (including HIV-induced forms), cerebral malaria, meningitis, ischemic and hemorrhagic stroke, cachexia secondary to infection or malignancy, cachexia secondary to acquired immune deficiency syndrome (AIDS), AIDS, ARC (AIDS related complex), keloid formation, scar tissue formation, inflammatory bowel disease, Crohn's disease, ulcerative colitis and pyresis.

Compounds of Formula (I) are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibiting-compounds of Formula (I). Such viruses include, but are not limited to HIV-1, HIV-2 and HIV-3, Cytomegalovirus (CMV), Influenza, adenovirus and the Herpes group of viruses, such as but not limited to, Herpes Zoster and Herpes Simplex. Accordingly, in a further aspect, this invention relates to a method of treating a mammal afflicted with a human immunodeficiency virus (HIV) which comprises administering to such mammal an effective TNF inhibiting amount of a compound of Formula (I) or a pharmaceutically acceptable salt thereof.

Compounds of Formula (I) may also be used in association with the veterinary treatment of mammals, other than in humans, in need of inhibition of TNF production. TNF mediated diseases for treatment in animals include disease states such as those noted above, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

The compounds of Formula (I) may also be used topically in the treatment of topical disease states mediated by or exacerbated by excessive cytokine production, such as by IL-1 or TNF respectively, such as inflamed joints, eczema, contact dermatitis psoriasis and other inflammatory skin conditions such as sunburn; inflammatory eye conditions including conjunctivitis; pyresis, pain and other conditions associated with inflammation. Periodontal disease has also been implemented in cytokine production, both topically and systemically. Hence, the use of compounds of Formula (I) to control the inflammation associated with cytokine production in such peroral diseases such as gingivitis and periodontitis is another aspect of the present invention.

Compounds of Formula (I) have also been shown to inhibit the production of IL-8 (Interleukin-8, NAP). Accordingly, in a further aspect, this invention relates to a method of inhibiting the production of IL-8 in a mammal in need thereof which comprises administering, to said mammal an effective amount of a compound of Formula (I) or a pharmaceutically acceptable salt thereof.

There are many disease states in which excessive or unregulated IL-8 production is implicated in exacerbating and/or causing the disease. These diseases are characterized by massive neutrophil infiltration such as, psoriasis, inflammatory bowel disease, asthma, cardiac and renal reperfusion injury, adult respiratory distress syndrome, thrombosis and glomerulonephritis. All of these diseases are associated with increased IL-8 production which is responsible for the chemotaxis of neutrophils into the inflammatory site. In contrast to other inflammatory cytokines (IL-1, TNF, and IL-6), IL-8 has the unique property of promoting neutrophil chemotaxis and activation. Therefore, the inhibition of IL-8 production would lead to a direct reduction in the neutrophil infiltration.

The compounds of Formula (I) are administered in an amount sufficient to inhibit a cytokine, in particular IL-1, IL-6, IL-8, IL-18 or TNF, production such that it is regulated down to normal levels, or in some case to subnormal levels, so as to ameliorate or prevent the disease state. Abnormal levels of IL-1, IL-6, IL-8, IL-18 or TNF, for instance in the context of the present invention, constitute: (i) levels of free (not cell bound) IL-1, IL-6, IL-8, IL-18 or TNF greater than or equal to 1 picogram per ml; (ii) any cell associated IL-1, IL-6, IL-8, IL-18 or TNF; or (iii) the presence of IL-1, IL-6, IL-8, IL-18 or TNF mRNA above basal levels in cells or tissues in which IL-1, IL-6, IL-8, IL-1 8 or TNF, respectively, is produced.

The discovery that the compounds of Formula (I) are inhibitors of cytokines, specifically IL-1. IL-6, IL-8, IL-18 and TNF is based upon the effects of the compounds of Formula (I) on the production of the IL-1, IL-8 and TNF in in vitro assays which are described herein or are well known to those skilled in the art.

As used herein, the term "inhibiting the production of IL-1 (IL-6, IL-8, IL-18 or TNF)" refers to:

a) a decrease of excessive in vivo levels of the cytokine (IL-1, IL-6, IL-8, IL-18 or TNF) in a human to normal or sub-normal levels by inhibition of the in vivo release of the cytokine by all cells, including but not limited to monocytes or macrophages;

b) a down regulation, at the genomic level, of excessive in vivo levels of the cytokine (IL-1, IL-6, IL-8, IL-18 or TNF) in a human to normal or sub-normal levels;

c) a down regulation, by inhibition of the direct synthesis of the cytokine (IL-1, IL-6, IL-8, IL-18 or TNF) or as a postranslational event to normal or sub-normal levels; or d) a down regulation, at the translational level, of excessive in vivo levels of the cytokine (IL-1, IL-6, IL-8, IL-18 or TNF) in a human to normal or sub-normal levels.

As used herein, the term "TNF mediated disease or disease state" refers to any and all disease states in which TNF plays a role, either by production of TNF itself, or by TNF causing another monokine to be released, such as but not limited to IL-1, IL-6, IL-8 or IL-18. A disease state in which, for instance, IL-1 is a major component, and whose production or action is exacerbated or secreted in response to TNF, would, therefore, be considered a disease state mediated by TNF.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epidermal keratinocytes and B-lymphocytes. Lymphokines are generally referred to as being produced by lymphocyte cells. Examples of cytokines include, but are not limited to Interleukin-1 (IL-1), Interleukin-6 (IL-6), Interleukin-8 (IL-8), Interleukin-18 (IL-18), Tumor Necrosis Factor-alpha (TNF-α) and Tumor Necrosis Factor beta (TNF-β).

As used herein, the term "cytokine interfering" or "cytokine suppressive amount" refers to an effective amount of a compound of Formula (I) which will cause a decrease in the in vivo levels of the cytokine to normal or sub-normal levels, when given to a patient for the treatment of a disease state which is exacerbated by, or caused by, excessive or unregulated cytokine production.

As used herein, the cytokine referred to in the phrase "inhibition of a cytokine for use in the treatment of a HIV-infected human" is a cytokine which is implicated in (a) the initiation and/or maintenance of T cell activation and/or activated T cell-mediated HIV gene expression and/or replication and/or (b) any cytokine-mediated disease associated problem such as cachexia or muscle degeneration.

As TNF-β (also known as lymphotoxin) has close structural homology with TNF-α (also known as cachectin) and since each induces similar biologic responses and binds to the same cellular receptor, both TNF-α and TNF-β are inhibited by the compounds of the present invention and thus are herein referred to collectively as "TNF" unless specifically delineated otherwise.

A relatively new member of the MAP kinase family, alternatively termed MAPK14, CSBP, p38 or RK, has been identified by several laboratories [See Lee, et al., *Nature*, Vol. 300, n(72), 739–746 (1994)]. Activation of this protein kinase via dual phosphorylation has been observed in different cell systems upon stimulation by a wide spectrum of stimuli, such as physicochemical stress and treatment with lipopolysaccharide or proinflammatory cytokines such as interleukin-1 and tumor necrosis factor. The cytokine biosynthesis inhibitors of the present invention, compounds of Formula (I) have been determined to be potent and selective inhibitors of CSBP/p38/RK kinase activity. These inhibitors are of aid in determining the signaling pathways involvement in inflammatory responses. In particular, a definitive signal transduction pathway can be prescribed to the action of lipopolysaccharide in cytokine production in macrophages. In addition to those diseases already noted herein, treatment of stroke, neurotrauma/CNS head injury, cardiac, brain and renal reperfusion injury, thrombosis, glomerulonephritis, diabetes and pancreatic β cells, multiple sclerosis, muscle degeneration, eczema, psoriasis, sunburn, and conjunctivitis are also included.

The cytokine inhibitors were subsequently tested in a number of animal models for anti-inflammatory activity. Model systems were chosen that were relatively insensitive to cyclooxygenase inhibitors in order to reveal the unique activities of cytokine suppressive agents. The inhibitors exhibited significant activity in many such in vivo studies. Additionally, the cytokine inhibitors of the present invention are effective in the collagen-induced arthritis model and inhibition of TNF production in the endotoxic shock model. In the latter study, the reduction in plasma level of TNF correlated with survival and protection from endotoxic shock related mortality. Also of great importance are the compound's effectiveness in inhibiting bone resorption in a rat fetal long bone organ culture system. Griswold, et al., (1988) *Arthritis Rheum.*, 31:1406–1412; Badger, et al., (1989) *Circ. Shock*, 27, 51–61, Votta, et al., (1994) *in vitro. Bone*, 15, 533–538; Lee, et al., (1993.). *B Ann. N. Y. Acad. Sci.*, 696, 149–170.

It is also recognized that both IL-6 and IL-8 are produced during rhinovirus (HRV) infections and contribute to the pathogenesis of common cold and exacerbation of asthma associated with HRV infection (Turner, et al., (1998), *Clin. Infec. Dis.*, Vol. 26, p. 840; Teren, et al. (1997), *Am. J. Respir. Crit. Care Med.*, Vol. 155, p. 1362; Grunberg, et al. (1997), *Am. J. Respir. Crit. Care Med.*, Vol. 156, p. 609 and Zhu, et al., *J. Clin. Invest.*, (1996), Vol. 97, p 421). It has also been demonstrated in vitro that infection of pulmonary epithelial cells with HRV results in production of IL-6 and IL-8 (Subauste, et al., *J. Clin. Invest.*, (1995), Vol. 96, p. 549). Epithelial cells represent the primary site of infection of HRV. Therefore, another aspect of the present invention is a method of treatment to reduce inflammation associated with a rhinovirus infection, not necessarily a direct effect of the virus itself.

Another aspect of the present invention involves the novel use of these p38/cytokine inhibitors for the treatment of chronic inflammatory or proliferative or angiogenic diseases, which are caused by excessive, or inappropriate angiogenesis.

Chronic diseases which have an inappropriate angiogenic component are various ocular neovascularizations, such as diabetic retinopathy and macular degeneration. Other chronic diseases which have an excessive or increased proliferation of vasculature are tumor growth and metastasis, atherosclerosis and certain arthritic conditions. Therefore, cytokine inhibitors will be of utility in the blocking of the angiogenic component of these disease states.

The term "excessive or increased proliferation of vasculature inappropriate angiogenesis" as used herein includes, but is not limited to, diseases which are characterized by hemangiomas and ocular diseases.

The term "inappropriate angiogenesis" as used herein includes, but is not limited to, diseases which are characterized by vesicle proliferation with accompanying tissue proliferation, such as occurs in cancer, metastasis, arthritis and atherosclerosis.

This invention also encompasses methods of treating or preventing disorders that can be treated or prevented by the inhibition of MAP in a mammal, preferably a human, comprising administering to said mammal an effective amount of a compound of the formula I.

Accordingly, the present invention provides a method of treating a p38 kinase mediated disease in a mammal in need thereof, preferably a human, which comprises administering to said mammal, an effective amount of a compound of Formula (I) or a pharmaceutically acceptable salt thereof.

Preferred p38 mediated diseases for treatment include, but are not limited to psoriatic arthritis, Reiter's syndrome, rheumatoid arthritis, gout, traumatic arthritis, rubella arthritis and acute synovitis, rheumatoid spondylitis, osteoarthritis, gouty arthritis and other arthritic conditions, sepsis, septic shock, endotoxic shock, gram negative sepsis, toxic shock syndrome, Alzheimer's disease, stroke, ischemic and hemorrhagic stroke, neurotrauma/closed head injury, asthma, adult respiratory distress syndrome, chronic obstructive pulmonary disease, cerebral malaria, meningitis, chronic pulmonary inflammatory disease, silicosis, pulmonary sarcostosis, bone resorption disease, osteoporosis, restenosis, cardiac reperfusion injury, brain and renal reperfusion injury, chronic renal failure, thrombosis, glomerularonephritis, diabetes, diabetic retinopathy, macular degeneration, graft vs. host reaction, allograft rejection, inflammatory bowel disease, Crohn's disease, ulcerative colitis, neurodegenerative disease, multiple sclerosis, muscle degeneration, diabetic retinopathy, macular degeneration, tumor growth and metastasis, angiogenic disease, rhinovirus infection, peroral disease, such as gingivitis and periodontitis, eczema, contact dermatitis, psoriasis, sunburn, and conjunctivitis.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

This invention also encompasses pharmaceutical compositions for the treatment of a condition selected from the group consisting of arthritis, psoriatic arthritis, Reiter's syndrome, gout, traumatic arthritis, rubella arthritis and acute synovitis, rheumatoid arthritis, rheumatoid spondylitis, osteoarthritis, gouty arthritis and other arthritic conditions, sepsis, septic shock, endotoxic shock, gram negative sepsis, toxic shock syndrome, Alzheimer's disease, stroke, neurotrauma, asthma, adult respiratory distress syndrome, cerebral malaria, chronic pulmonary inflammatory disease, silicosis, pulmonary sarcoidosis, bone resorption disease, osteoporosis, restenosis, cardiac and renal reperfusion injury, thrombosis, glomerularonephritis, diabetes, graft vs. host reaction, allograft rejection, inflammatory bowel disease, Crohn's disease, ulcerative colitis, multiple sclerosis, muscle degeneration, eczema, contact dermatitis, psoriasis, sunburn, or conjunctivitis shock in a mammal, including a human, comprising an amount of a compound of formula I effective in such treatment and a pharmaceutically acceptable carrier.

This invention also encompasses pharmaceutical compositions for the treatment of a condition which can be treated by the inhibition of MAP kinase in a mammal, including a human, comprising an amount of a compound of claim 1 effective in such treatment and a pharmaceutically acceptable carrier.

This invention also encompasses pharmaceutical compositions for the treatment of a condition which can be treated by the inhibition of p38 kinase in a mammal, including a human, comprising an amount of a compound of claim 1 effective in such treatment and a pharmaceutically acceptable carrier.

This invention also encompasses pharmaceutical compositions containing prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain.

The invention also encompasses sustained release compositions.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies (such as Remicade, CDP-870 and $D_2E_7$) and TNF receptor immunoglobulin molecules (such as Enbrel®), IL-1 inhibitors, receptor antagonists or soluble IL-1ra (e.g. Kineret or ICE inhibitors), COX-2 inhibitors (such as celecoxib, rofecoxib, valdecoxib and etoricoxib), metalloprotease inhibitors (preferably MMP-13 selective inhibitors), p2X7 inhibitors, α2δ inhibitors, low dose methotrexate, leflunomide, hydroxychloroquine, d-penicillamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flurbiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intraarticular therapies such as corticosteroids and hyaluronic acids such as hyalgan and synvisc.

The compounds of the present invention may also be used in combination with anticancer agents such as endostatin and angiostatin or cytotoxic drugs such as adriamycin, daunomycin, cis-platinum, etoposide, taxol, taxotere and alkaloids, such as vincristine, farnesyl transferase inhibitors, VegF inhibitors, and antimetabolites such as methotrexate.

The compounds of the invention may also be used in combination with antiviral agents such as Viracept, AZT, aciclovir and famciclovir, and antisepsis compounds such as Valant.

The compounds of the present invention may also be used in combination with cardiovascular agents such as calcium channel blockers, lipid lowering agents such as statins, fibrates, beta-blockers, Ace inhibitors, Angiotensin-2 receptor antagonists and platelet aggregation inhibitors.

The compounds of the present invention may also be used in combination with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, α2δ inhibitors, COX-2 inhibitors, propentofylline or metryfonate.

The compounds of the present invention may also be used in combination with osteoporosis agents such as roloxifene, droloxifene, lasofoxifene or fosomax and immunosuppressant agents such as FK-506 and rapamycin.

DETAILED DESCRIPTION OF THE INVENTION

Compounds of the formula I may be prepared according to the following reaction schemes and discussion. Unless otherwise indicated s, $R^1$ and $R^2$ and structural formula I (and Ia) in the reaction schemes and discussion that follow are as defined above.

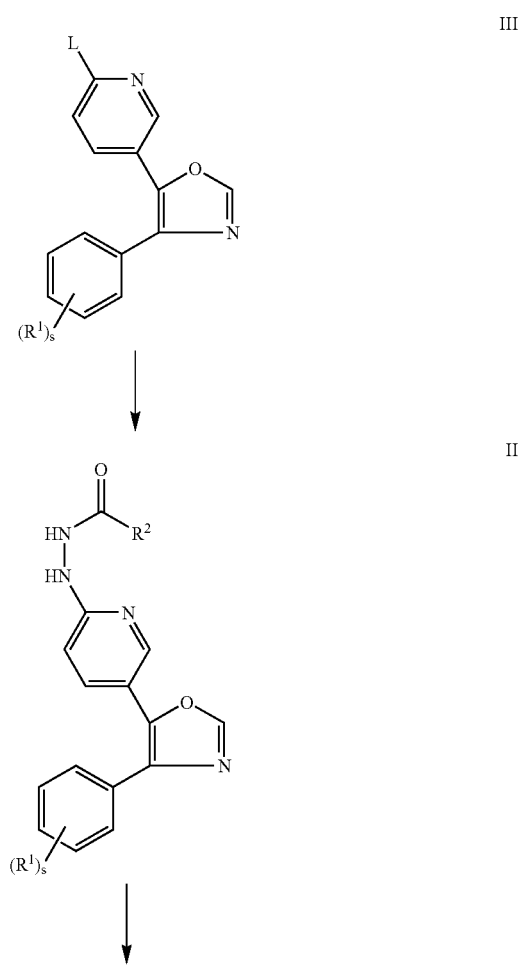

-continued
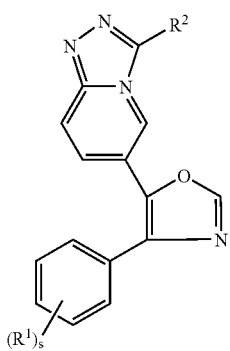
Scheme 2
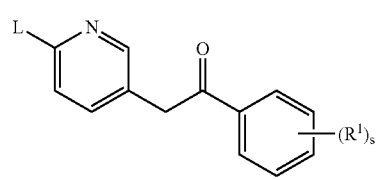
↓
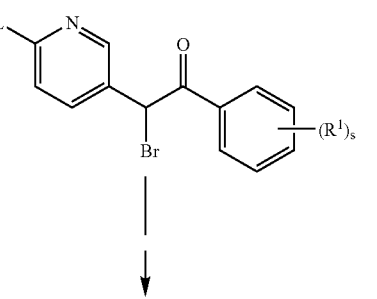
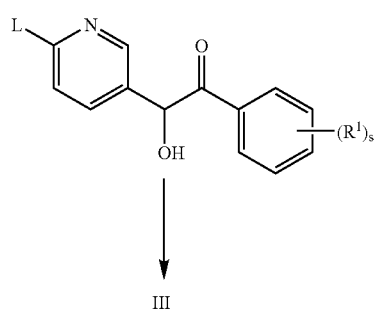
III
Scheme 3
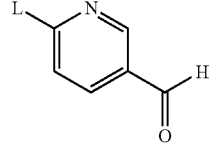   VIII
↓
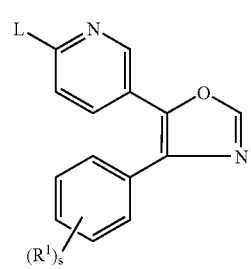   III
Scheme 4
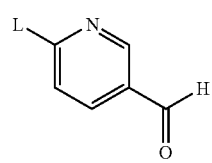   X
↓
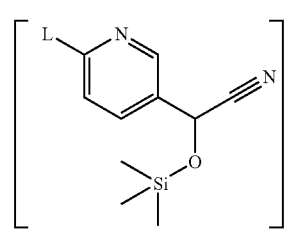   IX
↓
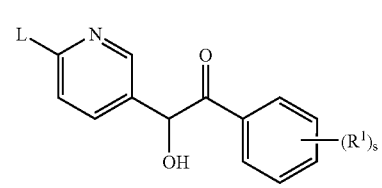   IV Scheme 5
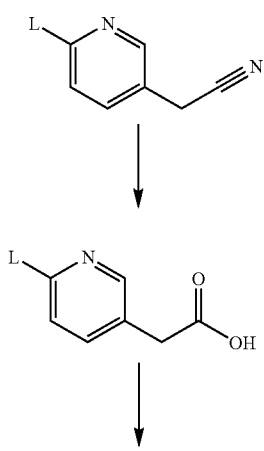
-continued
XIV
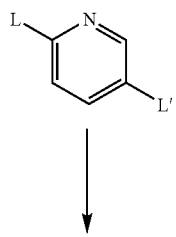
XI
XII
VI
Scheme 6
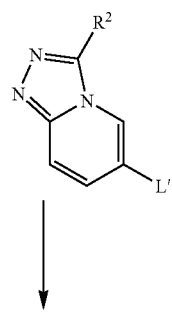
XX
XIX
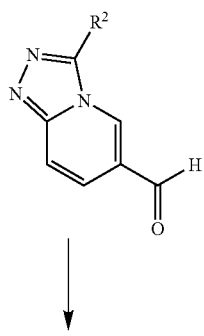
XVIII

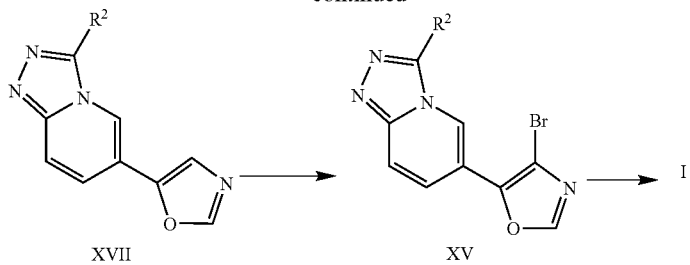

Scheme 1 refers to the preparation of compounds of the formula I in two steps from compounds of formula III. Referring to Scheme 1 compounds of the formula III, wherein L is a suitable leaving group such as fluoro, bromo, chloro or mesyl (MeSO$_2$), preferably bromo or chloro, are converted to the corresponding compound of formula II by reaction with hydrazine to form a hydrazino-pyridine, followed by reaction with an acylating reagent. The reaction of a compound of formula III with hydrazine is conducted in a polar solvent such as pyridine, ethanol or tert-butanol, or in neat hydrazine, preferably in neat hydrazine. The hydrazine reaction is conducted at a temperature between about 40° C. to about 80° C., preferably about 70° C. for about 10 minutes to about 60 minutes, preferably about 15 minutes. Acylation of the resulting hydrazino-pyridine to give compounds of the formula II is conducted with an acid chloride in the presence of a base such as triethylamine in a solvent such as dichloromethane, tetrahydrofuran, N,N-dimethylformamide, preferably dichloromethane, for a time period between about 10 minutes to about 120 minutes, preferably about 30 minutes, at a temperature of about 0° C. to about 22° C., preferably at about 0° C. Alternatively, the hydrazino-pyridine can be acylated with a carboxylic acid to give compounds of the formula II using amide coupling agents in a manner well known to one skilled in the art.

The compound of formula II can be converted to a compound of formula I using a suitable dehydrating agent or under conditions that promote cyclo-dehydration. Suitable dehydrating agents for the conversion of compounds of formula II to compounds of formula I include phosphorous oxychloride and dichlorotriphenylphosphorane, preferably phosphorous oxychloride. Reactions using phosphorous oxychloride are conducted in neat phosphorous oxychloride at a temperature between about 60° C. to about 110° C., for a time period between about 2 hours to about 16 hours. Reactions using dichlorotriphenylphosphorane are conducted in the presence of a base, such as triethylamine, in a polar solvent such as acetonitrile, at temperatures of about 60° C. and reflux for a time period from about 1 hour and about 8 hours.

Compounds of the formula III can be made according to the methods of Scheme 2.

Scheme 2 refers to the preparation of compounds of the formula III, which are intermediates useful in the preparation of compounds of the formula I, in Scheme 1. Referring to Scheme 2, a compound of the formula III, can be prepared from a compound of formula IV, by heating with formamide. The aforesaid reaction can be run at a temperature from about 100° C. to about 160° C. for a period from about 1 hour to about 12 hours, preferably at about 160° C. for about 3 hours.

The compound of formula IV is prepared from a compound of formula V by reaction with sodium methoxide, or sodium ethoxide, or sodium tert-butoxide, preferably sodium methoxide, in an alcohol solvent, such as methanol, ethanol, isopropanol, preferably methanol, at a temperature of 0° C. to 30° C., preferably at 22° C., for a period of time from 15 minutes to about 3 hours, preferably 30 minutes. The aforesaid reaction is followed by an aqueous acidic work-up.

The compound of formula V is prepared from a compound of formula VI by reaction with Br$_2$ in a polar solvent. Suitable solvents include acetic acid, chloroform or methylene chloride, preferably acetic acid. The aforesaid reaction is conducted at a temperature of about 0° C. to about 30° C. preferably at about 22° C. (room temperature) for a period from about 10 minutes to about 4 hours, preferably about 30 minutes.

The compounds of formula IV can also be prepared according to the methods of Scheme 4. The compounds of formula VI are prepared according to the methods of Scheme 5. Additional routes for the synthesis of compounds related to formula VI are described in the literature: Davies, I. W.; Marcoux, J.-F.; Corley, E. G.; Journet, M.; Cai, D.-W.; Palucki, M.; Wu, J.; Larsen, R. D.; Rossen, K.; Pye, P. J.; DiMichele, L.; Dormer, P.; Reider, P. J.; *J. Org. Chem.*, Vol. 65, pp. 8415–8420 (2000).

Scheme 3 refers to an alternate preparation of compounds of formula III, which are intermediates in Scheme 1. Referring to Scheme 3, compounds of the formula III, can be prepared from compounds of formula VIII by reaction with an isocyanide of formula

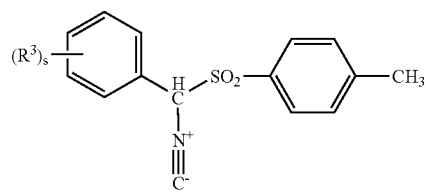

VII in the presence of a base. Suitable bases include potassium carbonate, triethylamine, 2,6-lutidine and piperazine, preferably 2,6-lutidine. Suitable solvents include polar solvents such as tetrahydrofuran, acetonitrile or N,N-dimethylformamide, preferably in acetonitrile or tetrahydrofuran. The aforesaid reaction may be run at a temperature between about 22° C. and about 70° C., preferably at about 22° C. for a period from about 2 hours to about 4 hours, followed by about 6 hours to about 10 hours at a temperature of about 70° C.

Compounds of formula VIII are known in the literature (when L is chloro see: Corey, E. J.; Loh, T-P.; AchyuthaRao, S.; Daley, D. C.; Sarshar, S., *J. Org. Chem.*, 1993, 58, 5600–5602) or can be prepared in a manner well known to one skilled in the art.

Compounds of the formula

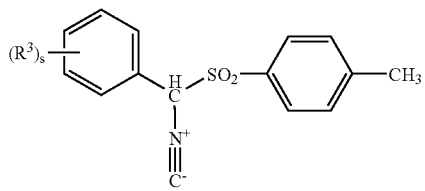

VII may be prepared by reacting a compound of the formula

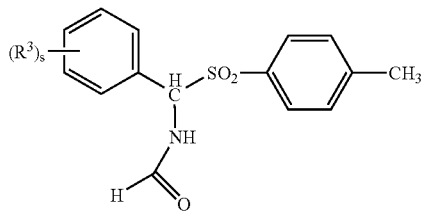

XXI with a dehydrating agent such as POCl$_3$, and a weak hindered base such as 2,6 lutidine or 2,4,6-trimethyl pyridine. Preferably the reaction is performed in the presence of a solvent such as tetrahydrofuran, dimethyl ether or methylene chloride. The aforesaid reaction may be run at a temperature between about −20° C. and about 50° C., preferably at about 0° C. to about room temperature for a period from about 2 hours to about 48 hours, preferably about 24 hours.

Scheme 4 refers to an alternate preparation of compounds of formula IV, which are intermediates in Scheme 2, useful in the preparation of compounds of formula I.

Compounds of formula IV can be prepared from compounds of formula IX by reaction with a suitably substituted Grignard reagent of the formula $(R^1)_s$-phenyl-M, wherein M is an activation group such as magnesium bromide or chloride (see for example: Jackson, W. R.; Jacobs, H. A.; Jayatilake, G. S.; Matthews, B. R.; Watson, K. G., *Aust. J. Chem.*, 1990, 43, 2045–2062). Reagents of the formula $(R^1)_s$-phenyl-M are commercially available or may be prepared by one skilled in the art.

The preparation and conversion of compounds of formula X into trimethylsilyl cyanohydrins of formula IX can be performed by methods known to those skilled in the art such as, for example, Pirrung, M.; Shuey, S. W.; *J. Org. Chem.*, 1994, 59, 3890–3897.

Scheme 5 refers to the preparation of compounds of the formula VI, which are intermediates for the preparation of compounds of formula III in Scheme 2. Referring to Scheme 5, a compound of the formula VI is prepared from a compound of formula XI by reaction with a Grignard reagent of the formula $(R^1)_s$-phenyl-M, wherein M is an activating group such as magnesium bromide or chloride in a solvent. Suitable solvents include tetrahydrofuran, dioxane, dimethylethyl ether or diethyl ether, preferably tetrahydrofuran. The aforesaid reaction is conducted at a temperature of about −78° C. to 0° C. for a period from about 10 minutes to about 24 hours preferably about 2 hours. Reagents of the formula $(R^1)_s$-phenyl-M are commercially available or may be prepared by one skilled in the art.

A compound of formula XI is prepared from a compound of formula XII by reaction with a hydroxylamine of the formula

XIII wherein $P^2$ and $P^3$ are independently $(C_1-C_6)$alkyl, preferably methyl, and an activating agent. Suitable activating agents include carbonyldiimidazole or oxalyl chloride, preferably carbonyldiimidazole. Suitable solvents include methylene chloride or dichloroethane.

Compounds of the formula XII are prepared from compounds of formula XIV by acid hydrolysis, such as by reaction with sulfuric acid/water (preferably 1:1) at a temperature of about 100° C. to about 120° C., preferably about 110° C. for a period from about 1 hour to about 6 hours, preferably about 4 hours. Alternatively, a compound of the formula XII is prepared by base hydrolysis, such as by reaction with lithium hydroxide in water at a temperature of about 23° C. to about 100° C., preferably at a temperature of about 80° C. for a period of about 4 to 10 hours.

Scheme 6 refers to an alternate preparation of compounds of formula I. Referring to Scheme 6, compounds of the formula I can be prepared from compounds of the formula XV by reaction with a boronic ester of the formula

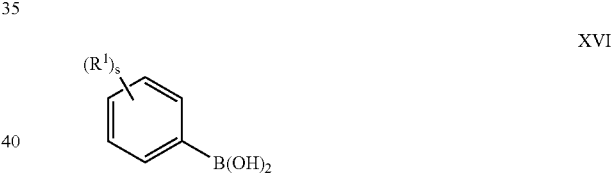

XVI a catalyst, and a base. Suitable catalysts include copper or palladium (such as palladium acetate (Pd(OAc)$_2$), tetrakis (triphenylphosphine) palladium (0) or Pd(dppf)Cl$_2$), preferably tetrakis(triphenylphosphine) palladium (0). Suitable bases include tertiary amine bases, such as triethylamine or pyridine, Na$_2$CO$_3$, sodium ethoxide, and K$_3$PO$_4$, preferably triethylamine. Suitable solvents include alcohols, such as methanol, ethanol and butanol, methylene chloride, dimethyl sulfoxide (DMSO) or tetrahydrofuran (THF), preferably ethanol. The aforesaid reaction is typically performed under an atmosphere of nitrogen gas at a temperature of about 10° C. to 85° C., preferably about 70° C. for about 6 to 72 hours. Palladium-catalyzed boronic acid couplings are described in Miyaura, N., Yanagi, T., Suzuki, A., *Syn. Comm.*, 1981, 11, 7, p. 513.

The compound of formula XV is prepared from a compound of formula XVII by reaction with a suitable bromination reagent such as phenyl trimethylammonium tribromide, N-bromosuccinimide, pyridinium bromide, perbromide, Br$_2$ or Br$_2$-Ph$_3$P, preferably N-bromosuccinimide. The bromination may be carried out in a reaction inert solvent such as N,N-dimethylformamide, diethyl ether or tetrahydrofuran, preferably dimethyl formamide. The aforesaid reaction is conducted at a temperature of about −78° C.

to about 40° C. preferably about −78° C. to about 0° C. for a time period between about 1 hour to about 16 hours. Preferably, the reaction is conducted in the presence of a base such as lithium bis(trimethylsilyl(amide)).

The compound of formula XVII is prepared from a compound of the formula XVIII by reaction with tosylmethylisocyanide in the presence of a base in a solvent. Suitable bases include alkali metal carbonates or hydroxide bases, preferably potassium carbonate. Suitable solvents for the aforesaid reaction include hexane, methylene chloride, alcohols, N,N-dimethylformamide (DMF), N,N-dimethylacetamide or N-methylpyrrolidinone (NMP) preferably methanol. The aforesaid reaction may be run at a temperature between about 30° C. and 180° C., preferably about 65° C., for about 30 minutes to 24 hours, preferably about 2 hours.

Alternatively, a compound of the formula I can be prepared from aldehydes of formula XVIII as described previously in Scheme 3 for the conversion of compounds of formula VIII to compounds of formula III.

Compounds of formula XVIII are prepared from compounds of formula XIX, wherein L' is bromo or iodo, by a formylation reaction. Suitable conditions for formylation include metal halogen exchange with isopropylmagnesium chloride in a solvent such as tetrahydrofuran at a temperature of about 0° C., for a period of time of about 30 minutes, followed by the addition of N,N-dimethylformamide at a temperature of about 0° C., followed by a period of time of about 2.5 hours at a temperature of about 50° C.

Compounds of formula XIX are prepared as described in the literature (Moran, D. B.; Morton, G. O.; Albright, J. D., *J. Heterocycl. Chem.*, Vol. 23, pp. 1071–1077 (1986)) or from compounds of formula XX as described in Scheme 1 for the conversion of compounds of formula III to compounds of formula I. Compounds of formula XX are commercially available.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

The activity of the compounds of the invention for the various disorders described above can be determined according to one or more of the following assays. All of the compounds of the invention that were tested had an $IC_{50}$ of less than 10 μM in the TNFα and MAPKAP in vitro assays and an $ED_{50}$ of less than 50 mg/kg in the in vivo TNFα assay.

The compounds of the present invention also possess differential activity (i.e. are selective for) for one or more p38 kinases (i.e. α, β, γ, and δ) or other MAP kinases. Certain compounds are selective for p38α over p38β, γ, and δ, other compounds are selective for p38β over p38α, γ, and δ, other compounds are selective for p38 α and β over p38 γ and δ. Selectivity is measured in standard assays as a $IC_{50}$ ratio of inhibition in each assay.

Inhibition of TNF-Alpha Production by Human LPS-Treated Monocytes

Mononuclear cells are isolated from heparinized blood (1.5 ml of 1000 units/ml heparin for injection, Elkins-Sinn, Inc. added to each 50 ml sample) using Accuspin System-Histopaque-1077 tubes (Sigma A-7054). Thirty-five milliliters of whole blood are added to each tube and the tubes are centrifuged at 2100 rpm for 20 minutes in a Beckman GS-6KR centrifuge with the brake off at room temperature. The mononuclear cells which collect at the interface are removed, diluted with Macrophage serum free medium (Gibco-BRL) (Medium) to achieve a final volume of 50 ml, and collected by centrifugation for 10 minutes. The supernatant is discarded and the cell pellet is washed 2 times with 50 ml of Medium. A sample of the suspended cells is taken before the second wash for counting. Based on this count, the washed cells are diluted with Medium containing 1% FBS to a final concentration of $2.7 \times 10^6$ cells/ml and 75 μl of the cell suspension is added to each well of a 96 well plate.

Compound Preparation

Compounds are routinely tested at final concentrations from 2 μM to 0.016 μM, but may be tested at other concentrations, depending on activity. Test agents are diluted with DMSO to a final concentration of 2 mM. From this stock solution, compounds are first diluted 1:25 (5 μl of 2 mM stock+120 μl Medium containing 400 ng/ml LPS and 1% FBS then 40 μl of this dilution is diluted with 360 μl of Medium with LPS. Serial dilutions (⅕) are performed by transferring 20 μl of this dilution to 80 μl of Medium containing both LPS and 0.4% DMSO, resulting in solutions containing 8 µM, 1.6 µM, 0.32 µM and 0.064 µM of test agent.

Assay

The assay is initiated by adding 25 µl of the diluted compounds to the mononuclear cell suspension and incubating the cells at 37 C and 5% $CO_2$ for 4 hours.

The 96-well plates are then centrifuged for 10 minutes at 2000 rpm at 4° C. in a Beckman GS-6KR centrifuge to remove cells and cell debris. A 90 µl aliquot of each supernatant is removed and transferred to a 96 well round bottom plate, and this plate is centrifuged a second time to insure that all cell debris is removed. 80 µl of the supernatant is removed and transferred to a new round bottom plate.

Supernatants are analyzed for TNF-α content using R&D ELISA. 25 µl of each sample is added to an ELISA well containing 25 µl of assay diluent RD1F and 75 µl of assay diluent RD5. The assay is run following kit directions except 100 µl of conjugate and substrate solutions are used.

Interpretation

The amount of TNF-α immunoreactivity in the samples is calculated as follows:

% Control=$(X-B)/(TOT-B) \times 100$ where X=$OD_{450}$ nm of the test compound well
B=$OD_{450}$ of Reagent Blank wells on the ELISA
Total=$OD_{450}$ of cells that were treated with 0.1% DMSO only.

MAPKAP Kinase-2 Assay

Monocyte Preparation

Mononuclear cells are collected from heparinized human blood as detailed above. The washed cells are seeded into 6-well cluster plates at a density of $1 \times 10^7$ cells/well (in 2 ml of Medium). The plates are incubated at 37° C. in a 5% $CO_2$ environment for 2 hours to allow adherence of the monocytes, after which time media supernatants containing non-adherent cells are removed by aspiration and 2 ml of fresh medium are added to each well. Plates are incubated overnight at 37° C. in a 5% $CO_2$ environment.

Cell Activation

Media are removed by aspiration. The attached cells are rinsed twice with fresh Medium, then 2 ml of D-MEM medium containing 10% heat inactivated FBS are added to each well. Test compounds are prepared as 30 mM stock solutions in DMSO and diluted to 1250, 250, 50, 10, 2, and 0.4 µM in D-MEM containing 1% DMSO and 10% FBS. To individual wells of the monocyte cultures, 20 µl of these test agent dilutions are added resulting in final test agent concentrations of 12.5, 2.5, 0.5, 0.1, 0.02 and 0.004 µM. After a 10 minute preincubation period, 20 µl of a 10 µg/ml LPS solution are added to each well and the plates are incubated at 37° C. for 30 minutes. Media subsequently are removed by aspiration, the attached monocytes are rinsed twice with phosphate buffered saline, then 1 ml of phosphate buffered saline containing 1% Triton X-100 (Lysis Buffer; also containing 1 Complete™ tablet [Boehringer #1697498] per 10 ml of buffer) is added to each well. The plates are incubated on ice for 10 minutes, after which the lysates are harvested and transferred to centrifugation tubes. After all samples are harvested, they are clarified by centrifugation (45,000 rpm for 20 minutes) and the supernatants recovered.

MAPKAP Kinase-2 Immunoprecipitation

5 µl of anti-MAPKAP kinase-2 antiserum (Upstate Biotechnology #06-534) is added to a microcentrifuge tube (1 tube for each of the above cell lysates) containing 1 ml of a 5% suspension of Protein G-Sepharose (Sigma #P3296) in PBS. These mixtures are incubated for 1 hour at 4° C. (with rocking) after which the beads, containing bound IgG, are recovered by centrifugation and washed twice with 1 ml of 50 mM Tris, pH 7.5, 1 mM EDTA, 1 mM EGTA, 0.5 mM orthovanadate, 0.1% 2-mercaptoethanol, 1% Triton X-100, 5 mM sodium pyrophosphate, 10 mM sodium β-glycerophosphate, 0.1 mM phenylmethylsulfonyl fluoride, 1 µg/ml leupeptin, 1 µg/ml pepstatin, and 50 mM sodium fluoride (Buffer A) by repeated centrifugation. An individual monocyte cell extract (prepared above) is then transferred to each tube containing a pellet of IgG-coated Protein G-Sepharose, and these mixtures are incubated for 2 hours at 4° C. (with rocking). The beads subsequently are harvested by centrifugation, and the resulting bead pellets are washed once with 0.5 ml of Buffer A containing 0.5 M NaCl, once with 0.5 ml of Buffer A, and once with 0.1 ml of a buffer composed of 20 mM MOPS, pH 7.2, 25 mM sodium β-glycerophosphate 5 mM EGTA, 1 mM orthovanadate, and 1 mM dithiothreitol (Buffer B).

MAPKAP Kinase-2 Activity Assessment

A kinase reaction mixture stock is prepared as follows: 2.2 µl of 10 mCi/ml γ[$^{32}$P]ATP, 88 µl of 1.3 µg/ml solution of MAPKAP Kinase-2 substrate peptide (Upstate Biotechnology #12-240), 11 µl of 10 mM ATP, 8.8 µl of 1 M $MgCl_2$, and 770 µl of Buffer B. To each of the immune complex-Protein G-pellets, 40 µl of the kinase reaction mixture are added and the tubes are incubated for 30 minutes at 30° C. The tubes then are clarified by centrifugation and 25 µl of each supernatant is spotted onto a P81 filter paper disk (Whatman #3698-023). After allowing all fluid to soak into the filter, each disk is placed into an individual well of 6-well cluster plates and the filters are washed sequentially with 2 ml of 0.75% phosphoric acid (3 washes/15 minutes each) and once with acetone (10 minutes). The filters then are air dried and transferred to liquid scintillation vials containing 5 ml of scintillation fluid. Radioactivity is determined in a liquid scintillation counter. The amount of radioactivity bound to the filter at each test agent concentration is expressed as a percentage of that observed from cells stimulated with LPS in the absence of a test agent.

In Vivo Inhibition of TNFα

Rats were weighed and dosed with vehicle (0.5% methyl cellulose, Sigma) or drug. One hour later, animals were injected i.p. with LPS (50 ug/rat, Sigma L-4130). Ninety minutes later, animals were sacrificed by asphyxiation with $CO_2$ and bled by cardiac puncture. Blood was collected in Vaccutainer tubes and spun for 20 minutes at 3000 rpm. Serum was assayed for TNFα levels using an ELISA (R&D Systems).

This invention also encompasses pharmaceutical compositions containing and methods of treating or preventing comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The compounds of formula I can also be formulated for sustained delivery according to methods well known to those of ordinary skill in the art. Examples of such formulations can be found in U.S. Pat. Nos. 3,538,214, 4,060,598, 4,173,626, 3,119,742, and 3,492,397, which are herein incorporated by reference in their entirety.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., inflammation) is 0.1 to 200 mg of the active ingredient per unit dose which could be administered, for example, 1 to 4 times per day.

Aerosol formulations for treatment of the conditions referred to above (e.g., adult respiratory distress syndrome) in the average adult human are preferably arranged so that each metered dose or "puff" of aerosol contains 20 µg to 1000 µg of the compound of the invention. The overall daily dose with an aerosol will be within the range 100 µg to 10 mg. Administration may be several times daily, for example 2, 3, 4 or 8 times, giving for example, 1, 2 or 3 doses each time.

Aerosol combination formulations for treatment of the conditions referred to above in the average adult human are preferably arranged so that each metered dose or "puff" of aerosol contains from about 0.01 mg to about 100 mg of the active compound of this invention, preferably from about 1 mg to about 10 mg of such compound. Administration may be several times daily, for example 2, 3, 4 or 8 times, giving for example, 1, 2 or 3 doses each time.

Aerosol formulations for treatment of the conditions referred to above in the average adult human are preferably arranged so that each metered dose or "puff" of aerosol contains from about 0.01 mg to about 2000 mg of an MAP kinase inhibitor, preferably from about 1 mg to about 200 mg of p38 kinase inhibitor. Administration may be several times daily, for example 2, 3, 4 or 8 times, giving for example, 1, 2 or 3 doses each time.

The following Examples illustrate the preparation of the compounds of the present invention. Melting points are uncorrected. NMR data are reported in parts per million ($\delta$) and are referenced to the deuterium lock signal from the sample solvent (deuteriochloroform unless otherwise specified). Mass Spectral data were obtained using a Micromass ZMD APCI Mass Spectrometer equipped with a Gilson gradient high performance liquid chromatograph. The following solvents and gradients were used for the analysis. Solvent A; 98% water/2% acetonirile/0.01% formic acid and solvent B; acetonitrile containing 0.005% formic acid. Typically, a gradient was run over a period of about 4 minutes starting at 95% solvent A and ending with 100% solvent B. The mass spectrum of the major eluting component was then obtained in positive or negative ion mode scanning a molecular weight range from 165 amu to 1100 amu. Specific rotations were measured at room temperature using the sodium D line (589 nm). Commercial reagents were utilized without further purification. THF refers to tetrahydrofuran. DMF refers to N,N-dimethylformamide. Chromatography refers to column chromatography performed using 32–63 mm silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure means that a rotary evaporator was used.

One of ordinary skill in the art will appreciate that in some cases, protecting groups may be required during preparation. After the target molecule is prepared, the protecting group can be removed by methods well known to those of ordinary skill in the art, such as described in Greene and Wuts, *Protective Groups in Organic Synthesis*, (2$^{nd}$ Ed., John Wiley & Sons, 1991).

Preparation 1

5-Bromo-pyridin-2-yl-hydrazine

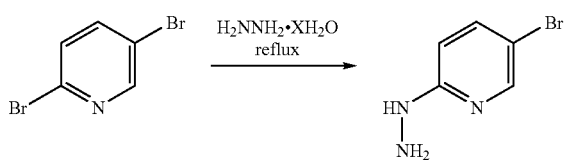

A 12 L three-necked round-bottomed flask equipped with a mechanical stirrer and a condenser, connected on top with a nitrogen bubbler and a thermometer, was charged with 2,5-dibromopyridine (442 g, 1.87 moles), hydrazine hydrate (55% wt., 1057 ml, 18.7 moles), poly(ethylene glycol) (average $M_n$ about 300, 1.87 L), 2-butanol (373 ml) and water (1.87 L). The mixture was heated at reflux for 29 hours. The heating source was removed and the mixture was stirred for an additional 20 hours. To the resulting slurry, cold water (2.2 L) was added. The slurry was stirred for an additional 30 minutes and filtered. The cake was washed with cold water (3×200 ml) and dried in a vacuum-oven (40° C.) for 48 hours. The title compound was obtained as off-white flakes (305 g, yield 87%).

GCMS(m/z): 187 (M+). H$^1$ NMR (400 MHz, CDCl$_3$): δ 8.14 (d, J=2.0 Hz, 1H), 7.55 (dd, J=8.7/2.0 Hz, 1H), 6.66 (d, J=8.7 Hz, 1H), 5.89 (brs, 1H), 3.65 (brs, 2H).

Preparation 2

6-Bromo-3-isopropyl-[1,2,4]triazolo(4,3-A)pyridine Hydrochloride

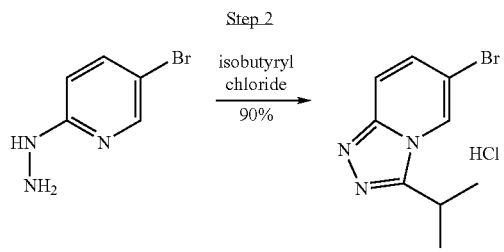

A 500 ml three-necked round-bottomed flask equipped with a mechanical stirrer and a condenser, connected on top to a nitrogen bubbler and a thermometer, was charged with 5-bromo-pyridin- 2-yl-hydrazine (43.4 g, 0.231 moles) and isobutyryl chloride (218 ml, 2.08 moles). The mixture was gently refluxed for 3 hours. The heating source was then replaced with an ice-water bath and the slurry cooled to room temperature. Hexane (220 ml) was added and the slurry stirred at room temperature for 15 minutes and filtered. The cake was washed with hexane (3×70 ml) and then dried in a vacuum-oven (35° C.) for 48 hours. The title compound was obtained as an off-white powder (58.96 g, yield 92.3%).

Preparation 3

6-Bromo-3-isopropyl-[1,2,4]triazolo(4,3-A)pyridine

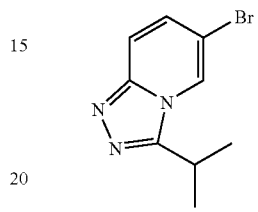

A 5 L three-necked round-bottomed flask, equipped with a mechanical stirrer and a thermometer, was charged with 6-bromo-3-isopropyl-[1,2,4]triazolo(4,3-a)pyridine hydrochloride (587.0 g, 2.12 moles), water (1.2 L) and dichloromethane (1.8 L). The biphasic mixture was cooled to 5 to 10° C. using an ice-water bath. Sodium hydroxide (1N aqueous solution) (2.15 L) was added over a period of 10 minutes. The mixture was stirred in the bath for 15 minutes. The organic layer was then isolated and the aqueous layer extracted with dichloromethane (600 mL). The combined organic extracts are washed with 1:1 brine-water (2 L) and dried (MgSO$_4$). Most of dichloromethane was removed by rotary evaporation. Ethyl acetate (800 ml) was then added. After removing about 400 ml of solvents, hexane (3.2 L) was added. The slurry was stirred in an ice-water bath for 2 hours and then filtered. The cake was washed with 9:1 hexane-ethyl acetate (3×150 ml) and dried in a vacuum-oven (30–35° C.) for 18 hours. The title compound (471.6 g, yield 92.5%), was obtained as a tan sandy powder.

H$^1$ NMR (400 MHz, CDCl$_3$): δ 8.06 (s, 1H), 7.64 (d, J=9.5 Hz, 1H), 7.24 (d, J=9.5 Hz, 1H), 3.33 (m, J=7.0 Hz, 1H), 1.52 (d, J=7.0 Hz, 6H).

Preparation 4

3-Isopropyl-[1,2,4]triazolo(4,3-A)-6-pyridinecarboxaldehyde

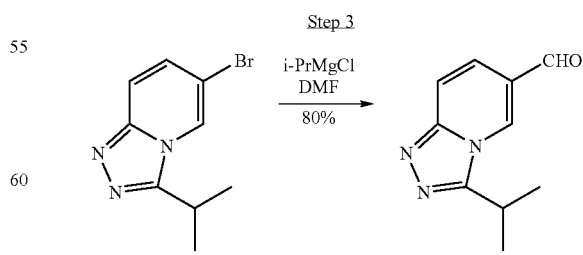

A 12 L three-necked round-bottomed flask, equipped with a mechanical stirrer, an addition funnel and a thermometer, was charged with 6-bromo-3-isopropyl-[1,2,4]triazolo(4,3- a)pyridine (200.0 g, 0.833 moles) and tetrahydrofuran (J. T. Baker, low water 2.0 L). The solution was cooled to −8° C. using an acetone/dry ice bath. A solution of isopropylmagnesium chloride in tetrahydrofuran (2.0M, 500 ml, 1.0 mole) was added via the addition funnel over a period of 55 minutes. The resulting brownish slurry was stirred between −4 to 0° C. for 30 minutes. Dimethylformamide (Aldrich, anhydrous, 155 ml, 2.0 moles) was added via an addition funnel over a period of 5 minutes. The cooling bath was replaced with a heating mantle and the addition funnel was replaced with a condenser. The slurry was heated to 55° C. and stirred at this temperature for 2 hours. The reaction mixture was cooled to 15° C. and dichloromethane (3 L) was added. The slurry was slowly poured into a stirred and ice-water cooled (15° C.) 10% by weight aqueous solution of citric acid (3 kg) over a period of 5 minutes. The biphasic mixture was stirred at 17 to 20° C. for 30 minutes. The organic layer was then isolated and the aqueous layer extracted with dichloromethane (5×1 L). The combined organic extracts were washed with 1:1 v/v brine-water (2 L), dried (MgSO$_4$) and concentrated. To the brownish residual solid was added ethyl acetate (800 ml). The slurry was stirred at room temperature for 10 minutes at which time hexane (800 ml) was added. The slurry was stirred at room temperature for 2 more hours and filtered. The cake was washed with 1:1 v/v hexane-ethyl acetate (3 x 150 ml) and dried in a vacuum-oven (30–35° C.) for 18 hours. The title compound was obtained as a yellowish sandy powder (126.6 g, yield 80%).

GCMS(m/z): 189 (M+). H$^1$ NMR (400 MHz, CDCl$_3$): δ 10.00 (s, 1 H), 8.49 (s, 1 H), 7.79 (d, J=9.5 Hz, 1H), 7.68 (d, J=9.5 Hz, 1H), 3.47 (m, J=7.0 Hz, 1H), 1.56 (d, J=7.0 Hz, 6H).

Preparation 5 p-Toluenesulfinic Acid

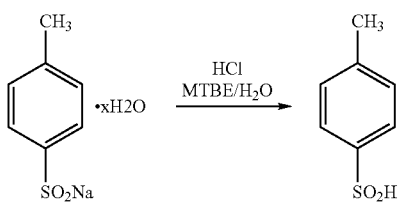

A 5 L three-necked round-bottomed flask, equipped with a mechanical stirrer and a thermometer, was charged with p-toluenesulfinic acid, sodium salt hydrate (Aldrich, CH$_3$C$_6$H$_4$SO$_2$Na.xH$_2$O, 392.0 g), tap water (2 L) and methyl t-butyl ether (2 L). The mixture was stirred at room temperature for 10 minutes at which time hydrochloric acid (37% wt. in water, 142 ml, 1.2 moles) was added over a period of 5 minutes. The biphasic mixture was stirred at room temperature for 30 minutes. The organic layer was then isolated and the aqueous layer extracted with methyl t-butyl ether (500 mL). The combined organic extracts were concentrated to a residual white semi-solid, which was diluted with toluene (700 ml). Most of solvents were removed and hexane (1.8 L) was then added. The slurry was stirred at room temperature for 30 minutes and filtered. The cake was washed with hexane (2×300 ml) and dried in a vacuum-oven (30–35° C.) for 3 hours. The product, p-toluenesulfinic acid (240.0 g,), was obtained as a white powder.

Preparation 6

N-[(2,5-Difluoro-phenyl)-(Toluene-4-Sulfonyl)-methyl]-formamide

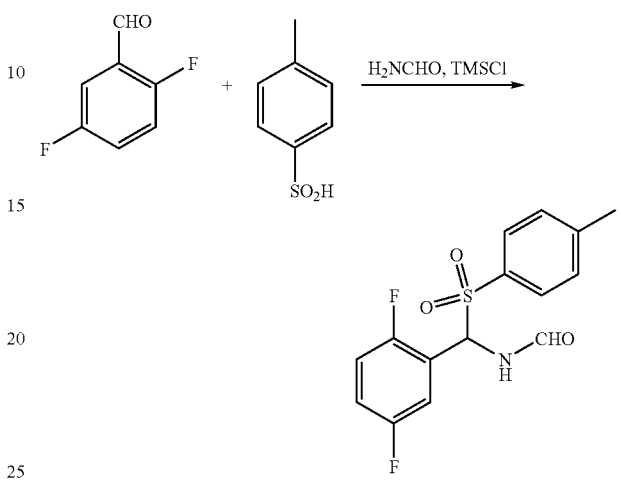

A 5 L three-necked round-bottomed flask, equipped with a mechanical stirrer, a condenser and a thermometer, was charged with 2,5-difluorobenzaldehyde (142.11 g, 1 mole). Toluene (500 ml), acetonitrile (500 ml), formamide (99.3 ml, 2.5 moles) and chlorotrimethylsilane (139.6 ml, 1.1 moles) were added respectively. The cloudy mixture was heated to 50° C. and stirred at this temperature for 7 hours. p-Toluenesulfinic acid (218.68 g, 1.4 moles) was added. The mixture was stirred at 50° C. for 6 hours and then 13 hours at room temperature. Methyl t-butyl ether (1.8 L) and water (1.7 L) were then added. The mixture was stirred at room temperature for 15 minutes at which time the organic layer was separated. The aqueous layer was extracted with methyl t-butyl ether (500 ml). Most of the solvents were removed from the combined organic extracts. To the residual white semi-solid, hexane (1 L) and water (1 L) were added. The slurry was stirred at room temperature for 30 minutes and filtered. The cake was washed with hexane (2×200 ml) and dried in a vacuum-oven (30° C.) for 18 hours. The product, N-[(2,5-Difluoro-phenyl)-(toluene-4-sulfonyl)-methyl]-formamide (258.3 g, yield 79%,), was obtained as a white powder.

Preparation 7

[α-(p-Toluenesulfonyl)-2,5-difluorobenzyl]isonitrile

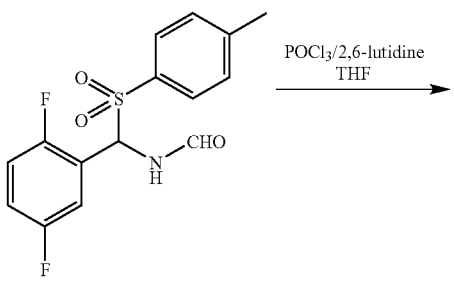

-continued

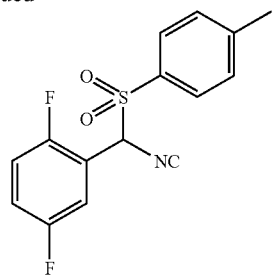

A 5 L three-necked round-bottomed flask, equipped with a mechanical stirrer, an addition funnel and a thermometer, was charged with N-[(2,5-Difluoro-phenyl)-(toluene-4-sulfonyl)-methyl]-formamide (207.0 g, 0.636 moles) and tetrahydrofuran (J. T. Baker, low water, 1.5 L). Phosphorous oxychloride (118.6 ml, 1.27 moles) was quickly poured into the reaction mixture (less than 5 minutes). The mixture was stirred at room temperature for 10 minutes and then cooled to 4° C. using an ice/water bath. 2,6-Lutidine (445 ml, 3.82 moles) was added via the addition funnel over a period of 30 minutes. The cooling bath was then removed and the mixture was stirred at room temperature for 18 hours. The reaction mixture was poured into a stirred and ice-water cooled solution of 1.5 kg of ice and 1.1 L of saturated aqueous sodium bicarbonate (NaHCO$_3$). The mixture was then extracted with ethyl acetate (2 L plus 1.5 L). The combined organic extracts were washed with 1N aqueous hydrochloric acid (3 L), saturated aqueous NaHCO$_3$ (3 L) and brine (3 L); and then dried (MgSO4). After removing all solvents, isopropanol (1.8 L) was added to the residual brownish solid. The resulting slurry was stirred at room temperature for 2 hours. Water (0.9 L) was added and the slurry was stirred for additional 30 minutes at room temperature and then filtered. The cake was washed with 2:1 isopropanol-water (2×500 ml) and dried in a vacuum-oven (30° C.) for 48 hours. The product, [α-(p-Toluenesulfonyl)-2,5-difluorobenzyl]isonitrile (133.4 g, yield 68%,), was obtained as a brownish powder.

H$^1$ NMR (400 MHz, CDCl$_3$): δ, 7.7 (d, J=8.3 Hz, 2H) 7.41 (d, J=8.3 Hz, 2H), 7.18 (m, 3H), 5.91 (s, 1H), 2.50 (s. 3H).

Preparation 8

[α-(p-Toluenesulfonyl)-2,5-difluorobenzyl]isonitrile

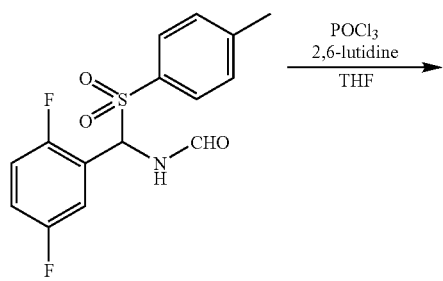

-continued

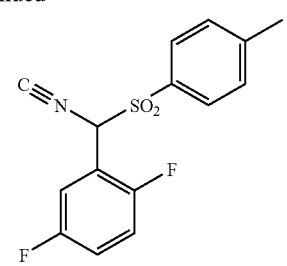

To a clean a dry nitrogen purged acetone boiled out 100 gallon glass lined reactor was charged, 7.9 Kg of N-[(2,5-Difluoro-phenyl)-(toluene-4-sulfonyl)-methyl]-formamide (24, moles), 16 gallons of tetrahydrofuran and 7.8 Kg of phosphorous oxychloride (51 moles). The batch was allowed to stir at 20° C. for 30 minutes and then cooled to 3.5° C. To the batch was added 15.8 Kg of 2,6-lutidine (146 moles) over 15 minutes. The reaction mixture was allowed to warm to 23° C. and was stirred for 17 hours at 23° C. The reaction was judged complete by HPLC and was charged to a 40 gallon solution of 10% sodium bicarbonate at 22° C., and the contents were allowed to stir for 30 minutes. To the batch was then added 25 gallons of ethyl acetate and the layers were separated. The water layer was backwashed with 9 gallons of ethyl acetate and the product rich ethyl acetate combined with the first wash. The product rich ethyl acetate layers were added to a 10% citric acid solution (20 gallons) and then stirred. The organic layer was checked by HPLC for 2,6 lutidine and then separated. The organic layer was washed with 10 gallons of saturated NaCl and dried over 7.9 Kg of magnesium sulfate. The drying agents were removed by filtration and the cake was washed with 4 gallons of ethyl acetate. The ethyl acetate layer was concentrated to 7 gallons under vacuum at an internal temperature of 24° C. The batch was then added to 11 gallons of IPO at 21° C. and allowed to granulate at 4° C. for 12 hours. The product was isolated via filtration and washed with 4 gallons of 5° C. IPO. The product was then dried at 34° C. for 22 hours with nitrogen bleed to recover 5.0 Kg of the title compound (66% yield).

Preparation 9

6-[Oxazol-5-yl]-3-isopropyl-[1,2,4]triazolo[4,3-a]pyridine

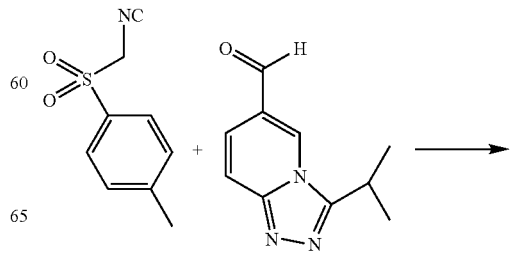

-continued

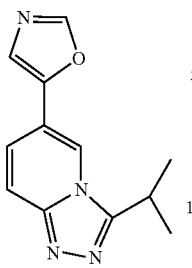

To a clean dry 5 liter round bottomed flask equipped with a mechanical stirrer, nitrogen bubbler, heating mantle, temperature controller, and condenser, was charged 3-isopropyl-[1,2,4]triazolo(4,3-a)-6-pyridinecarboxaldehyde (140.9 grams, 0.745 moles), potassium carbonate (133.8 grams, 0.968 moles), tosylmethyl isocyanide (146.9 grams, 0.745 moles), and methanol (2114 ml). This mixture was heated at reflux and stirred for 1.5 to 2.0 hours at 65 to 70° C. Assay by HPLC showed the reaction to be complete. The pot was concentrated atmospherically to about one third of original volume. Water (1409 ml), was added and the pot further concentrated to a pot temperature of 65 to 66° C. to remove the remaining methanol. After cooling, the desired product was extracted with methylene chloride (1409 ml). The extraction was repeated twice with methylene chloride (2 times 705 ml). The combined extracts were atmospherically concentrated and displaced with Isopropyl alcohol (420 ml). A thick slurry formed. Hexanes (1690 ml) were added and the slurry allowed to granulate for 12 to 16 hours at 20 to 25° C. The solids were collected by vacuum filtration, washed with hexanes, and dried to yield 111.45 grams, 97.8% purity (HPLC), 65.5% of theory.

$^1$H NMR (CDCl$_3$, 400 MHz) δ 8.23 (s, 1H), 7.98 (s, 1H), 7.82 (d, 1H, J=9.5 Hz), 7.46–7.43 (m, 2H), 3.43 (sept, 1H, J=7.05 Hz), 1.56 (d, 6H, J=7.05 Hz); MS 229 (M$^{30}$+1). cl
Preparation 10

6-[4-Bromo-oxazol-5-yl]-3-isopropyl-[1,2,4]triazolo[4,3-a]pyridine

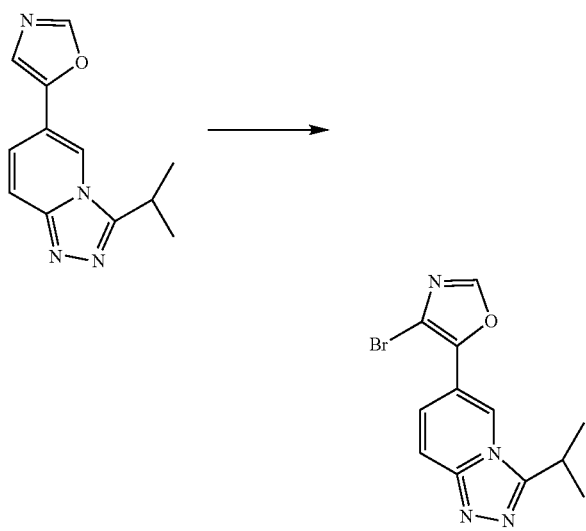

A clean, dry, 1 liter 4 neck round bottom flask equipped with mechanical stirrer, temperature probe, and purged with nitrogen, was charged with 6-[oxazol-5-yl]-3-isopropyl-[1,2,4]triazolo[4,3-a]pyridine (45.2 grams 0.198 moles) and dimethylformamide (271 ml). The pot was cooled below −60° C. with a dry ice/acetone bath. Lithium bis(trimethylsilyl)amide, 1 molar solution in tetrahydrofuran (198 ml 0.198 moles), was added, keeping the temperature below −60° C. After the addition was complete, the pot was further cooled to below −70° C. and stirred for 1 hour. While stirring, a solution of N-bromosuccinimide (35.24 g 0.198 moles) and dimethylformamide (105 ml), were stirred in a separate 500 ml round bottom flask under nitrogen. After the one hour stir at −70° C., the solution of N-bromosuccinimide and dimethylformamide was slowly added to the anion keeping the temperature below −70° C. After the addition, the reaction was continued for one hour below −70° C. The batch was then warmed to room temperature and quenched into methylene chloride (452 ml) and 1N sodium hydroxide (452 ml). The organic layer was then separated. The aqueous layer was extracted a second time with methylene chloride (135 ml). The combined organic phase was washed with 1N sodium hydroxide (452 ml) and saturated brine solution (452 ml). The organic phase was then dried over magnesium sulfate (50 grams) and concentrated/displaced with isopropyl ether (226 ml) to a temperature of 42° C. A thick slurry formed upon cooling. The solids were granulated at 20 to 25° C. for two hours, filtered, washed with isopropyl ether (50 ml), and dried to afford 53.0 grams of light yellow solids, 96.4% purity (HPLC), 87% of theory.

$^1$H NMR (CDCl$_3$, 400 MHz) δ 8.56 (s, 1H), 7.95 (s, 1H), 7.85 (d, 1H, J=9.5 Hz), 7.77 (d, 1H, J=9.5 Hz), 3.43 (sept, 1H, J=7.05 Hz), 1.56 (d, 6H, J=7.05 Hz); MS: 310, 309, 308, 307 (M$^+$+1).

EXAMPLE 1

3-Isopropyl-6-[4-(2,4,5-trifluoro-phenyl)-oxazol-5-yl]-[1,2,4]triazolo[4,3-a]pyridine

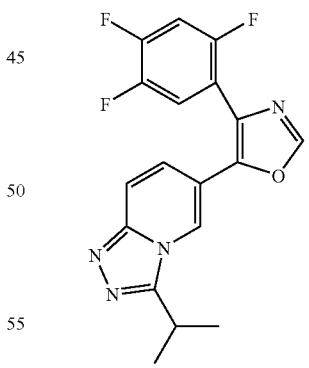

A) 5-Bromo-pyridine-2-yl-hydrazine

A mixture of 2,5-dibromopyridine (44.2 g, 0.187 moles), hydrazine hydrate (55% by weight, 105.7 mL, 1.87 mol), poly(ethylene glycol) (187.0 mL), 2-butanol (37.3 mL) and water (187.0 mL) under nitrogen is refluxed gently for 29 hours. The mixture is cooled and stirred for 20 hours. To the resulting slurry, cold water (220.0 mL) is added. The slurry is stirred for an additional 30 minutes and filtered. The cake is washed with cold water (3×) and dried in a vacuum-oven (40–45° C.) for 48 hours. The title compound (30.5 g, 87%) may be obtained as off-white flakes.

B) 6-Bromo-3-isopropyl-[1,2,4]triazolo(4,3-a)pyridine

A mixture of 5-bromo-pyridine-2-yl-hydrazine (4.34 g, 23.1 mmol) and isobutyryl chloride (21.8 mL, 0.208 mol) is refluxed gently for 3 hours. The mixture is cooled to room temperature. Hexane (22.0 mL) is added and the slurry is stirred at room temperature for 15 minutes and filtered. The cake is washed with hexane (3×) and dried in a vacuum-oven (30–35° C.) for 48 hours. The product (5.90 g, yield 92.3%) is obtained as an off-white powder. A biphasic mixture of the product (5.87 g, 21.2 mmol), water (12.0 mL) and dichloromethane (18.0 mL) is cooled to 5–10° C. A 1N aqueous solution of NaOH (21.5 mL) is added over a period of 10 minutes. The mixture is stirred in the bath for 15 minutes. The organic layer is isolated and the aqueous layer extracted with dichloromethane (2×). The combined organic extracts are washed with 1:1 brine-water and dried (MgSO$_4$). Most of the dichloromethane is removed in vacuo. Ethyl acetate (8.0 mL) is added. After removing about half of the solvents, hexane is added. The slurry is stirred in an ice-water bath for 2 hours and filtered. The cake is washed with 9:1 hexane-Ethyl acetate (3×) and dried in a vacuum-oven (30–35° C.) for 18 hours. The title compound may be obtained as a sandy tan powder (4.72g, 92.5%).

C) 3-Isopropyl-[1,2,4]triazolo(4,3-a)-6-pyridinecarboxaldehyde

To a cooled (−8° C.) solution of 6-bromo-3-isopropyl-[1,2,4]triazolo(4,3-a)pyridine (2.0 g, 8.33 mmol) and THF (20.0 mL) is added a solution of isopropylmagnesium chloride in THF (2.0M, 5.0 mL, 10.0 mmol) over 55 minutes, maintaining the temperature between −8 to 0° C. The resulting brownish slurry is stirred between −4 to 0° C. for 30 minutes. DMF (1.55 mL, 20.0 mmol) is then added over 5 minutes, and the slurry heated to 55° C. for 2 hours. The reaction mixture is cooled to 15° C. and dichloromethane (30.0 mL) added. The slurry is slowly poured into a stirring, cooled 10 percent by weight aqueous solution of citric acid (30.0 g) over a period of 5 minutes. The biphasic mixture is stirred at 17–20° C. for 30 minutes. The organic layer is separated and the aqueous layer extracted with dichloromethane (5×). The combined organic extracts are washed with 1:1 volume/volume brine-water (20.0 mL), dried (MgSO$_4$) and concentrated to a brownish residual solid. Ethyl acetate (8.0 mL) is added, the slurry stirred at room temperature for 10 minutes and then hexane (8.0 mL) is added. The slurry is stirred at room temperature for 2 hours and filtered. The cake is washed with 1:1 v/v hexane-Ethyl acetate (3×) and dried in a vacuum-oven (30–35° C.) for 18 hours. The title compound may be obtained as a yellowish sandy powder (1.27 g, 80%).

D) p-Toluenesulfinic Acid

A mixture of p-toluenesulfinic acid, sodium salt hydrate (39.2 g), water (200.0 mL) and methyl t-butyl ether (MTBE, 200.0 mL) is stirred at room temperature for 10 minutes, then hydrochloric acid (37% weight in water, 14.2 mL, 0.12 mol) is poured in over a period of 5 minutes. The biphasic mixture is stirred at room temperature for 30 minutes. The layers are separated and the aqueous layer extracted with methyl t-butyl ether (MTBE) (50.0 mL). The combined organic extracts are concentrated in vacuo (bath temperature below 35° C.) to a white semi-solid. Toluene (70.0 mL) is added to the residual solid. Most of solvents are removed and hexane (180.0 mL) is added. The slurry is stirred at room temperature for 30 minutes and filtered. The cake is washed with hexane (2×) and dried in a vacuum-oven (30–35° C.) for 3 hours. The product, p-toluenesulfinic acid may be obtained as a white powder (24.0 g).

E) N-[(2,4,5-Tifluoro-phenyl)-(toluene-4-sulfonyl)-methyl]-formamide

To 2,4,5-trifluorobenzaldehyde (10.0 g, 62.4 mmol) is added toluene (60.0 mL), acetonitrile (60.0 mL), formamide (6.2 mL, 156.2 mmol) and chlorotrimethylsilane (8.8 mL, 68.8 mmol) in order. The mixture is stirred at ambient temperature for 1 hour, then p-toluenesulfinic acid (14.6 g, 93.6 mmol) is added, and the mixture stirred at 50° C. for 18 hours. The reaction is cooled to ambient temperature, then filtered. The filtrate is concentrated in vacuo to a yellow oil. Silica gel chromatography yields the title compound as a white solid (13.77 g, 64%).

F) [α-(p-Toluenesulfonyl)-2,4,5-tifluorobenzyl]isonitrile

To a mixture of N-[(2,4,5-tifluoro-phenyl)-(toluene-4-sulfonyl)-methyl]-formamide (13.7 g, 39.9 mmol) and THF (140.0 mL) is added POCl$_3$ (7.5 mL, 79.8 mmol) over a period of 5 minutes, and the resulting mixture stirred at room temperature for 1 hour. The reaction is then cooled to 0° C. and 2,6-lutidine (28.0 mL, 239.4 mmol) is added over 30 minutes, maintaining the temperature less than 12° C. The cooling bath is removed and the mixture stirred at room temperature for 18 hours. The reaction mixture is poured into a stirred, ice water cooled solution of 10% aqueous NaHCO$_3$. The mixture is extracted with ethyl acetate (3×). The combined organic extracts are washed with 1N aqueous hydrochloric acid, saturated aqueous NaHCO$_3$, brine and dried (Na$_2$SO$_4$). Silica gel chromatography, followed by recrystallization from ethyl acetate/hexane yields the title compound as an orange solid (3.37 g, 26%).

G) 6-[4-(2,4,5-trifluoro-phenyl)-oxazol-5-yl]-3-isopropyl-[1,2,4]triazolo[4,3-a]pyridine A mixture of [α-(p-Toluenesulfonyl)-2,4,5-tifluorobenzyl]isonitrile (172.0 mg, 0.528 mmol), 3-isopropyl-[1,2,4]triazolo(4,3-a)-6-pyridinecarboxaldehyde (100.0 mg, 0.528 mmol), potassium carbonate (95.0 mg, 0.686 mmol) and acetonitrile (2.0 mL) was heated at 70° C. for 22 hours. The reaction mixture was cooled to room temperature and poured into water. The aqueous layer was extracted with CHCl$_3$ (3×). The extracts were washed with brine, dried over sodium sulfate, filtered, and the filtrate concentrated in vacuo to a dark solid. Silica gel chromatography afforded the title compound as a tan solid (90.0 mg, 48%). LCMS (m/z) 359 (M+1). $^1$H NMR (400 MHz, CDCl$_3$) δ 8.24 (s, 1H), 8.08–8.10 (m, 2H), 7.57–7.63 (m, 1H), 7.50 (d, 1H, J=9.6 Hz), 7.02–7.08 (m, 1H), 3.38–3.41 (m, 1H), 1.53 (d, 6H, J=6.7 Hz).

EXAMPLE 2

3-Isopropyl-6-[4-(2,3,4-trifluoro-phenyl)-oxazol-5-yl]-[1,2,4]triazolo[4,3-a]pyridine

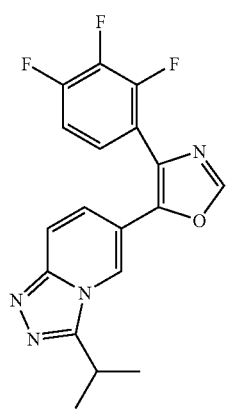

This compound was prepared in an analogous manner to Example 1, starting with 2,3,4-trifluorobenzaldehye in Step E. LCMS (m/z) 359 (M+1). $H^1$ NMR (400 MHz, CDCl$_3$) δ 8.30 (s, 1H), 8.20 (d, 1H, J=7.8 Hz), 8.15–8.16 (m, 1H), 7.62 (d, 1H, J=7.8 Hz), 7.50 (s, 1H), 7.21 (d, 1H, J=7.3 Hz), 3.44 (d, 1H, J=6.7 Hz), 1.56–1.62 (m, 6H).

EXAMPLE 3

3-Isopropyl-6-[4-(2,3,5-trifluoro-phenyl)-oxazol-5-yl]-[1,2,4]triazolo[4,3-a]pyridine

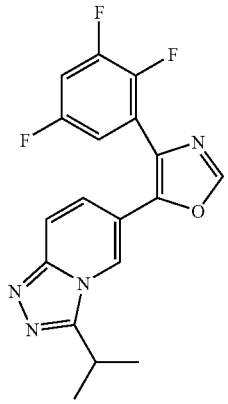

This compound was prepared in an analogous manner to Example 1, starting with 2,3,5-trifluorobenzaldehyde in Step E. LCMS (m/z) 359 (M+1).

EXAMPLE 4

3-Isopropyl-6-[4-(2,4,6-trifluoro-phenyl)-oxazol-5-yl]-[1,2,4]triazolo[4,3-a]pyridine

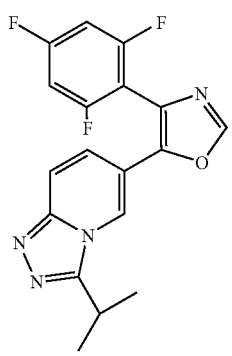

This compound was prepared in an analogous manner to Example 1, starting with 2,4,6-trifluorobenzaldehye in Step E. LCMS (m/z) 359 (M+1).

EXAMPLE 5

3-Isopropyl-6-[4-(3,4,5-trifluoro-phenyl)-oxazol-5-yl]-[1,2,4]triazolo[4,3-a]pyridine

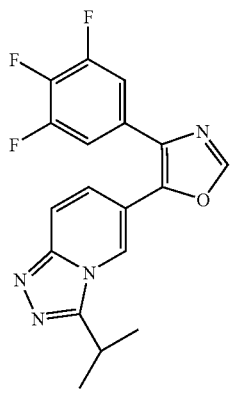

This compound was prepared in an analogous manner to Example 1, starting with 3,4,5-trifluorobenzaldehye in Step E. LCMS (m/z) 359 (M+1).

EXAMPLE 6

3-tert-Butyl-6-[4-(2,4,5-trifluoro-phenyl)-oxazol-5-yl]-[1,2,4]triazolo[4,3-a]pyridine

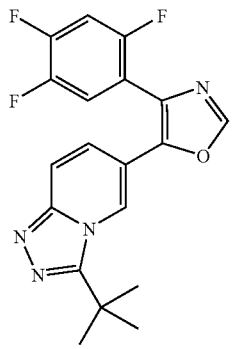

This compound was prepared in an analogous manner to Example 1, starting with trimethylacetyl chloride in Step B. LCMS (m/z) 373 (M+1).

What is claimed is:

1. A compound of the formula

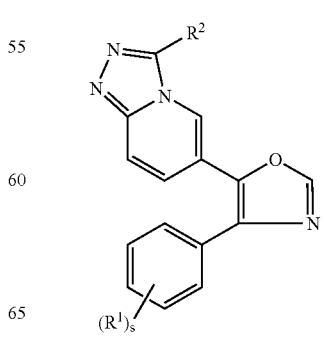

I wherein $R^1$ is fluoro;
s is three;
$R^2$ is $(C_1-C_6)$alkyl optionally substituted by one or two moieties independently selected from the group consisting of halo, $(C_1-C_6)$alkyl, hydroxy, $(C_1-C_6)$alkoxy, and $C_1-C_6$ alkyl-(C=O)—O—;
or a pharmaceutically acceptable salt thereof.

2. A compound according to claim 1 wherein $R^2$ is $(C_1-C_6)$alkyl optionally substituted with one or two groups independently selected from halo, hydroxy, and $(C_1-C_6)$ alkoxy.

3. A compound according to claim 1, wherein $R^2$ is optionally substituted ethyl, isopropyl, isobutyl, t-butyl or sec-butyl.

4. A compound according to claim 1, wherein the compound has the formula

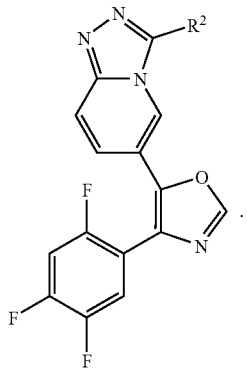

Ia

5. A compound according to claim 1, wherein $R^2$ is $(C_1-C_6)$alkyl, optionally substituted with halo or hydroxy.

6. A compound according to claim 1, wherein $R^2$ is ethyl, isopropyl, isobutyl, t-butyl or sec-butyl; optionally substituted with a halo or hydroxy.

7. A compound according to claim 1, wherein $R^2$ is $(C_1-C_4)$alkyl.

8. A compound according to claim 1, wherein said compound is 3-Isopropyl-6-[4-(2,4,5-trifluoro-phenyl)-oxazol-5-yl]-[1,2,4]triazolo[4,3-a]pyridine.

9. A compound according to claim 1, wherein said compound is 3-tert-Butyl-6-[4-(2,4,5-trifluoro-phenyl)-oxazol-5-yl]-[1,2,4]triazolo[4,3-a]pyridine.

10. A compound according to claim 1, wherein said compound is selected from the group consisting of:

3-Isopropyl-6-[4-(2,3,4-trifluoro-phenyl)-oxazol-5-yl]-[1,2,4]triazolo[4,3-a]pyridine;

3-Isopropyl-6-[4-(2,3,5-trifluoro-phenyl)-oxazol-5-yl]-[1,2,4]triazolo[4,3-a]pyridine;

3-Isopropyl-6-[4-(2,4,6-trifluoro-phenyl)-oxazol-5-yl]-[1,2,4]triazolo[4,3-a]pyridine; and 3-Isopropyl-6-[4-(3,4,5-trifluoro-phenyl)-oxazol-5-yl]-[1,2,4]triazolo[4,3-a]pyridine.

11. A pharmaceutical composition comprising an amount of a compound according to claim 1 and a pharmaceutically acceptable carrier.

* * * * *